(12) United States Patent
Bennett et al.

(10) Patent No.: US 11,021,643 B2
(45) Date of Patent: Jun. 1, 2021

(54) ORGANOCLAY COMPOSITION AND ITS USE

(71) Applicants: BYK USA, Inc., Wallingford, CT (US); BYK-Chemie GmbH, Wesel (DE)

(72) Inventors: Richard William Bennett, Seguin, TX (US); Patricia M. Bauer, Gonzales, TX (US); René Nagelsdiek, Wesel (DE)

(73) Assignees: BYK USA, Inc., Wallingford, CT (US); BYK-Chemie GmbH, Wesel (DE)

( * ) Notice: Subject to any disclaimer, the term of this patent is extended or adjusted under 35 U.S.C. 154(b) by 366 days.

(21) Appl. No.: 16/313,574

(22) PCT Filed: Jul. 6, 2017

(86) PCT No.: PCT/EP2017/066988
§ 371 (c)(1),
(2) Date: Dec. 27, 2018

(87) PCT Pub. No.: WO2018/011058
PCT Pub. Date: Jan. 18, 2018

(65) Prior Publication Data
US 2019/0316020 A1    Oct. 17, 2019

Related U.S. Application Data

(60) Provisional application No. 62/360,542, filed on Jul. 11, 2016.

(51) Int. Cl.
| | | |
|---|---|---|
| *C09K 8/36* | (2006.01) | |
| *C09C 1/42* | (2006.01) | |
| *C09K 8/34* | (2006.01) | |
| *C09K 8/80* | (2006.01) | |

(52) U.S. Cl.
CPC ............... *C09K 8/36* (2013.01); *C09C 1/42* (2013.01); *C09K 8/34* (2013.01); *C09K 8/80* (2013.01)

(58) Field of Classification Search
None
See application file for complete search history.

(56) References Cited

U.S. PATENT DOCUMENTS

| | | | |
|---|---|---|---|
| 3,959,158 A | 5/1976 | Stanford et al. | |
| 4,816,551 A | 3/1989 | Oehler et al. | |
| 5,180,802 A | 1/1993 | Hartman et al. | |
| 5,429,999 A * | 7/1995 | Nae ................. | C09K 8/32 501/146 |
| 6,339,048 B1 | 1/2002 | Santhanam et al. | |
| 6,462,096 B1 * | 10/2002 | Dino ............... | C01B 33/44 501/146 |
| 6,787,592 B1 | 9/2004 | Powell et al. | |
| 7,326,750 B1 | 2/2008 | Isik et al. | |
| 7,371,360 B2 | 5/2008 | Wenzel et al. | |
| 7,786,189 B2 | 8/2010 | Maruo et al. | |
| 7,799,742 B2 | 9/2010 | Dino | |
| 7,867,614 B2 | 1/2011 | Seeling et al. | |
| 7,871,962 B2 | 1/2011 | Patel et al. | |
| 8,470,727 B2 | 6/2013 | Nip | |
| 9,284,201 B2 | 3/2016 | Kambala et al. | |
| 10,626,314 B1 * | 4/2020 | Bennett ............ | C09K 8/36 |
| 2009/0308599 A1 * | 12/2009 | Dusterhoft ........ | E21B 28/00 166/249 |
| 2010/0305008 A1 * | 12/2010 | Dino ............... | C09K 8/32 507/131 |
| 2016/0186034 A1 * | 6/2016 | Mainye ............ | C09K 8/32 507/103 |
| 2016/0298015 A1 | 10/2016 | Gupta et al. | |
| 2017/0198190 A1 * | 7/2017 | Maxey ............. | E21B 43/16 |

FOREIGN PATENT DOCUMENTS

| | | |
|---|---|---|
| CA | 1051859 A | 4/1979 |
| EP | 0 229 912 A2 | 7/1987 |
| EP | 0 259 266 A2 | 3/1988 |
| EP | 0 428 393 A1 | 5/1991 |
| EP | 1 138 740 A1 | 10/2001 |
| JP | 2006335823 A | 12/2006 |
| WO | 95/09135 A1 | 4/1995 |
| WO | 2016048332 A1 | 3/2016 |

OTHER PUBLICATIONS

International Search Report dated Oct. 18, 2017 PCT/EP2017/066988.
Written Opinion dated Oct. 18, 2017 PCT/EP2017/066988.

\* cited by examiner

*Primary Examiner* — John J Figueroa
(74) *Attorney, Agent, or Firm* — Curatolo Sidoti Co., LPA; Salvatore A. Sidoti

(57) ABSTRACT

An organoclay composition which is a mineral clay or mineral clay mixture that has been treated with at least organic quaternary ammonium compound and a synergist comprising (i) an amine salt of a trimer acid, and (ii) an amine salt of a monocarboxylic fatty acid. The monocarboxylic fatty acid may be (a) at least one saturated carboxylic acid; and/or (b) at least one unsaturated carboxylic acid.

25 Claims, No Drawings

ORGANOCLAY COMPOSITION AND ITS USE

CROSS REFERENCE TO RELATED APPLICATIONS

This application is a national stage application of International Application No. PCT/EP2017/066988, filed 6 Jul. 2017, which claims priority from U.S. Provisional Patent Application No. 62/360,542, filed 11 Jul. 2016, which applications are incorporated herein by reference.

Provided are organophilic phyllosilicates (hereinafter referred to as "organoclays"), and more specifically organoclays prepared from particular mineral clays or mixtures of clays which have been treated with a combination of quaternary ammonium or phosphonium compound(s) and a synergist. The resultant organoclays are useful as functional additives for non-aqueous fluid systems, where they may confer desired rheological properties, or may confer other mechanical or physical properties sought for such systems.

In one illustrative use, the rheological properties of organoclays are of importance in drilling fluids. Drilling fluids, also known as circulating fluids, are used in rotary drilling of geological formations containing hydrocarbons. Drilling fluids may also be used in rotary drilling of geological formations containing other materials, such as water. There are three main categories of drilling fluids: water-based drilling fluids; non-aqueous or oil-based drilling fluids; and gaseous drilling fluids. Drilling fluids may also be known as "drilling muds". The focus of one particular use of the present subject matter is in non-aqueous/oil-based drilling fluids; for simplicity, use of the terms "drilling fluid" or "drilling fluids" hereinafter refers to non-aqueous/oil-based drilling fluids, unless specified otherwise. However, it is contemplated that the present subject matter may be useful with other drilling fluids.

In the course of drilling an oil, gas or water well by means of rotary drilling tools, the drill pipe and bit are rotated to drill out the borehole. A so-called "drilling fluid" or "drilling mud" is circulated downwardly through the hollow drill stem pipe and bit nozzles to the bottom of the borehole and then flows back up the well to the surface through the annular space between the drill stem pipe and the interior of the borehole (the walls of the wellbore). This drilling fluid comprises a suspension of solid material in a liquid medium and may contain other added agents. As the drilling fluid flows back up the wellbore, it carries drill cuttings, which are removed before recirculation and reuse of the drilling fluid. The drilling fluid lubricates and cools the drill bit, and suspends and carries cuttings out of the borehole. In order to perform these and other functions the drilling fluid should desirably have certain physical characteristics. These include a shear-thinning viscosity that enables it to be pumped and circulated. Also the fluid should have sufficient gel strength that cuttings will remain suspended in the borehole if circulation of the fluid pumping is stopped, as for example by a mechanical failure. The drilling fluid performs a number of additional functions, including: providing hydrostatic pressure; supporting the weight of the drill pipe and/or casing; coating the wellbore surface to prevent leakage and/or at least partial collapse of the wellbore; and preventing flow of material into or out of the wellbore.

The subject organoclay composition is further useful in other primarily non-aqueous fluid systems, such as hydraulic fracturing fluids, organic grease compositions, lubricants, metal working fluids, inks, oil/solvent-based paint formulations, coating, sealant and adhesive materials, unsaturated polyester systems, unsaturated polyester/styrene resin systems, vinyl ester systems, acrylic resins, epoxy resin systems, polyurethane resin systems, nanocomposites, moulding compounds, cosmetics, cleaners, personal care formulations and home care formulations, among others.

The subject organoclay composition includes a synergistic combination of a mineral clay which has been treated with at least an organic quaternary ammonium or phosphonium compound or a precursor thereof and a synergist comprising (i) an amine salt of a trimer acid, and (ii) an amine salt of a monocarboxylic fatty acid. The monocarboxylic fatty acid may be: (a) at least one saturated carboxylic acid; and/or (b) at least one unsaturated carboxylic acid.

The clays used may be any of those which have substantial base-exchange capacity, detailed below.

To obtain the desired organoclays, a mineral clay or a mixture of mineral clays may be treated or reacted with functional organic compounds, as is well known to those skilled in the art. The amount of organic compound used will be dependent on the reactivity of the clay(s) used, but may be from about 20 to 300 milliequivalents of a surfactant such as an organic ammonium or phosphonium salt, for example, per 100 grams of clay. The reactions may be conducted in water and the treated clay may be separated and dried.

More generally, organoclays may be prepared by wet or dry processes, which may depend on the desired end-use, and/or the amount and/or type of surfactant treatment. Wet-processed organoclays may yield faster and have greater thermal stability than dry-processed organoclays, because inert materials are removed and surface treatment of the wet-processed organoclays may be more complete. Additionally, the synergist can be post added to an existing organoclay by methods such as but not limited to mixing, blending, extruding and/or grinding. The synergist may be added as a dry component or in a liquid carrier and/or solvent.

In certain embodiments, the processing of the subject organoclays includes dispersing the clay(s) in water at concentrations of about 1.5% to about 10% based on the weight of the dispersion, in certain embodiments, about 3% to about 8% based on the weight of the dispersion, with refining to remove impurities and with adequate shear to exfoliate/debundle the clay particles. Small amounts of a dispersing aid, such as tetrasodium pyrophosphate (TSPP), can be used to further disperse the clay(s). Further processing includes adding the organic quaternary ammonium or phosphonium compounds to convert the hydrophilic clays into hydrophobic organoclays with subsequent filtration and drying to remove the water. In certain embodiments, the organoclays are converted into a milled powder as a final form while in other embodiments the final form is spray-dried beads.

In one procedure for preparing the organoclay composition, the raw clay minerals are crushed, ground, slurried in water and refined to remove grit and other impurities, such as by screening, cycloning and/or centrifuging. Each of the clay minerals may then be subjected as a dilute (such as 1 to 6 weight-% solids) aqueous slurry to high shearing in a suitable mill, such as a homogenizing mill of the type wherein high speed fluid shear of the slurry is effected by passing the slurry at high velocities through a narrow gap, across which a high pressure differential is maintained. This type of action can, e.g., be effected in the well-known Manton-Gaulin "MG" mill, which device is sometimes referred to as the "Gaulin homogenizer". U.S. Pat. Nos. 4,664,842 and 5,110,501 provide details of such mill and its use.

Other instruments which can provide high shearing of the clay mineral materials may be used as well. The use of high shear is useful for processing montmorillonite, for example, and acts to "debundle" the otherwise "bundled" type of mineral structures, such as those which exist in sepiolite mineral material.

If more than one clay material is being mixed to form the organoclay composition, following the high shear step, the clay component slurries may be mixed with one another. Alternatively, the two or more clay components can be intermixed in a single slurry before the latter is subjected to the high shear step. Following such steps the (single) slurry is intermixed with the quaternary ammonium salt(s), for example, and the synergist, sequentially (either one first) or in combination, after which the slurry is dewatered, and the synergist/quaternary ammonium-treated clay is filtered and dried to provide a dry organoclay product, as a milled powder or spray dried beads.

According to the present disclosure there is provided an organoclay composition comprising a mineral clay which has been treated with at least one organic quaternary ammonium or phosphonium compound and a synergist comprising (i) an amine salt of a trimer acid, the trimer acid having from about 30 to about 72 carbon atoms; and (ii) an amine salt of a monocarboxylic fatty acid, the monocarboxylic fatty acid having from about 6 to about 30 carbon atoms, optionally wherein the monocarboxylic fatty acid comprises at least one of: (a) at least one saturated carboxylic acid; or (b) at least one unsaturated carboxylic acid.

The term trimer acid refers to trimerized fatty acids, or compositions comprising trimerized fatty acids. In certain embodiments, the trimer acid may have from about 36 to about 72 carbon atoms, or optionally from about 36 to about 66 carbon atoms, or further optionally from about 42 to about 60 carbon atoms, or further optionally from about 48 to about 54 carbon atoms.

In certain embodiments, the trimer acid may comprise at least one of trimers of hexadecatrienoic acid, α-linolenic acid, rumelenic acid, stearidonic acid, α-parinaric acid, β-parinaric acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid (nisinic acid), α-eleostearic acid, β-eleostearic acid, catalpic acid, punicic acid, linoleic acid, 10E,12Z-octadeca-9,11-dienoic acid, γ-linolenic acid, pinolenic acid, α-calendic acid, β-calendic acid, jacaric acid, eicosadienoic acid, dihomo-γ-linolenic acid, podocarpic acid, arachidonic acid, bosseopentaenoic acid, docosadienoic acid, docosatetraenoic acid, docosapentaenoic acid, tetracosatetraenoic acid, tetracosapentaenoic acid, 5-dodecenoic acid, 7-tetradecenoic acid, palmitoleic acid, vaccenic acid, rumenic acid, paullinic acid, 15-docosenoic acid, 17-tetracosenoic acid, oleic acid, talloil fatty acid, elaidic acid, gondoic acid, mead acid, erucic acid, nervonic acid, myristoleic acid, sapienic acid, or combinations thereof.

The monocarboxylic fatty acid component of the synergist may have from about 8 to about 26 carbon atoms, or optionally from about 12 to about 20 carbon atoms, or further optionally from about 16 to about 18 carbon atoms.

In certain embodiments, the monocarboxylic fatty acid is a tall oil fatty acid which may have from about 16 to about 22 carbon atoms, or optionally from about 16 to about 20 carbon atoms, or further optionally from about 16 to about 18 carbon atoms.

In particular embodiments, the monocarboxylic fatty acid comprises at least one of myristoleic acid, sapienic acid, linoleic acid, linoelaidic acid, α-linolenic acid, docosa- hexaenoic acid, abietic acid, pimaric acid, tall oil fatty acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, hexadecatrienoic acid, α-linolenic acid, rumelenic acid, stearidonic acid, α-parinaric acid, β-parinaric acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid (nisinic acid), α-eleostearic acid, β-eleostearic acid, catalpic acid, punicic acid, linoleic acid, 10E,12Z-octadeca-9,11-dienoic acid, γ-linolenic acid, pinolenic acid, α-calendic acid, β-calendic acid, jacaric acid, eicosadienoic acid, dihomo-γ-linolenic acid, podocarpic acid, arachidonic acid, bosseopentaenoic acid, docosadienoic acid, docosatetraenoic acid, docosapentaenoic acid, tetracosatetraenoic acid, tetracosapentaenoic acid, 5-dodecenoic acid, 7-tetradecenoic acid, palmitoleic acid, vaccenic acid, rumenic acid, paullinic acid, 15-docosenoic acid, 17-tetracosenoic acid, oleic acid, elaidic acid, gondoic acid, mead acid, erucic acid, or nervonic acid.

In certain embodiments, the amine of the synergist component (i) and/or component (ii) may be a saturated or unsaturated monoamine having from about 3 to about 90 carbon atoms, or optionally from about 3 to about 54 carbon atoms, or further optionally from about 8 to about 37 carbon atoms, or further optionally from about 10 to about 24 carbon atoms, or further optionally from about 14 to about 20 carbon atoms. In some embodiments, the amine of the synergist component (i) and component (ii) are the same.

In particular embodiments, the amine may comprise a monoamine of the general formula (I):

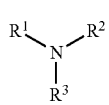

wherein:
$R^1$ represents a saturated or unsaturated, linear or branched hydrocarbon group having from about 1 to about 30 carbon atoms, or optionally from about 6 to about 24 carbon atoms, or further optionally from about 8 to about 22 carbon atoms; and
$R^2$ and $R^3$ are the same or different from each other and $R^1$, and represent hydrogen or saturated or unsaturated, linear or branched hydrocarbon groups having from about 1 to about 30 carbon atoms, or optionally from about 6 to about 24 carbon atoms, or further optionally from about 8 to about 22 carbon atoms.

In some embodiments, the amine comprises a monoamine of general formula (I) in which $R^1$ represents a saturated or unsaturated, linear or branched hydrocarbon group having from about 12 to about 20 carbon atoms, and $R^2$ and $R^3$ represent hydrogen. In some embodiments, the amine may comprise a monoamine in which $R^1$ represents a saturated or unsaturated, linear or branched hydrocarbon group having from about 12 to about 20 carbon atoms, and $R^2$ and $R^3$ represent a hydrocarbon group having 1 to 7, optionally 1 to 4, further optionally 1 to 2 carbon atoms.

In certain embodiments, the amine may comprise at least one of n-propylamine, isopropylamine, n-butylamine, isobutylamine, amylamine, n-pentylamine, isopentylamine, hexylamine, 2-ethylhexylamine, octyl-amine, 6-methyl-2-heptaneamine, neopentylamine, decyl-amine, tridecylamine, octadecylamine, oleylamine, cocoyl amine, stearyl amine, tallo amine, soya amine, or mixtures of $C_8$-$C_{22}$ alkylamines.

In certain embodiments, the amine of the synergist component (i) and component (ii) are different. In these embodiments, transsalinization (i.e., ion exchange) may occur between the component (i) and the component (ii) in situ.

In certain embodiments, the weight ratio of the synergist component (i):component (ii) is from about 95:5 to about 5:95, or optionally from about 90:10 to about 10:90, or further optionally from about 80:20 to about 30:70, or further optionally from about 70:30 to about 50:50, or further optionally from about 65:35 to about 55:45.

The amount of synergist which may be used to treat the clay mineral material may range from about 2 to about 30 grams, optionally about 4 to about 30 grams, further optionally from about 5 to about 15 grams, and in certain embodiments, about 7.5 to about 12.5 grams, based upon 100 grams of the dry mineral clay or mineral clay mixture.

In some embodiments, the synergist is used in a liquid formulation which further comprises at least one additional material (such as a carrier and/or solvent). The at least one additional material may comprise at least one of aliphatic hydrocarbons, aromatic hydrocarbons, araliphatic hydrocarbons, aliphatic alcohols, aromatic alcohols, araliphatic alcohols, glycols, glycol ethers, or alkylene carbonates. In certain embodiments, the hydrocarbon(s) may comprise at least one of diesel oil, mineral oil, or synthetic oil. In certain embodiments, the alcohol(s) may comprise at least one alkanol, such as ethanol. In certain embodiments, the alkylene carbonate(s) may comprise at least one of ethylene carbonate, propylene carbonate, or glycerine carbonate.

The subject organoclay composition is derived from a mineral clay (natural or synthetic) which may comprise at least one of a smectite clay; a hormite clay, optionally sepiolite, attapulgite (also known as palygorskite) or mixture of sepiolite and attapulgite (palygorskite); a mixture of hormite clay and smectite clay, optionally a mixture of sepiolite and/or attapulgite, and smectite clay; illite; vermiculite; or zeolites or mixtures thereof. The smectite clay may be selected from hectorite, montmorillonite, bentonite, beidellite, saponite, stevensite, Fuller's earth or mixtures thereof. In some embodiments, the smectite clay comprises bentonite, such as swelling bentonite.

By way of illustration but not limitation, the organoclay may be derived from a mineral clay that comprises substantially a single clay form or a mixture of clay forms, such as substantially bentonite or montmorillonite, substantially hectorite, substantially sepiolite or attapulgite, mixtures of sepiolite or attapulgite and bentonite, mixtures of sepiolite or attapulgite and montmorillonite, mixtures of sepiolite or attapulgite and hectorite, mixtures of sepiolite or attapulgite and saponite, and the like. By "substantially" is meant that the mineral clay is not an intentional mixture of clay forms, but may contain other clay forms as naturally occurring impurities. According to one embodiment "substantially" means more than 50 wt. %, in particular more than 75 wt. %, further more particularly more than 85 wt. % based on the total weight of the mineral clay.

The organic quaternary ammonium or phosphonium compound used to treat the mineral clay or mineral clay mixture to form the subject organoclay composition may comprise at least one of alkyl, alkenyl, aryl, aralkyl, alkylaryl, alkoxylated, or nitrogen- or phosphor-containing heterocycle, quaternary ammonium or phosphonium compound or salt or precursor thereof, or combinations thereof. For purposes of this disclosure, quaternary phosphonium based compounds or salts are defined as within the definition of quaternary ammonium compound.

The alkyl or alkenyl quaternary ammonium compound may comprise a salt having formula (II):

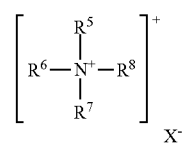

(II)

wherein N is nitrogen; $X^-$ comprises an anion such as at least one of chloride, methyl sulfate, acetate, iodide, bromide, nitrate, hydroxide, phosphate, methoxysulfate and mixtures thereof; $R^5$ comprises a linear or branched, saturated or unsaturated aliphatic (i.e. alkyl, alkenyl or alkynyl) hydrocarbon group having from 8 to 30 carbon atoms; and, $R^6$, $R^7$, and $R^8$ are independently selected from: a) linear or branched, saturated or unsaturated aliphatic hydrocarbon, having from 1 to about 30 carbon atoms; b) allyl, vinyl, or other alkenyl or alkynyl groups possessing reactive unsaturation and having from 2 to about 30 carbon atoms; c) hydrogen; and d) aryl, aralkyl or alkylaryl, such as phenyl, phenyl substituted moieties, benzyl and substituted benzyl moieties.

In certain embodiments, $R^5$ may comprise $C_{12}$ to $C_{22}$ linear or branched saturated alkyl groups, in other embodiments $C_{14}$-$C_{22}$ linear or branched saturated alkyl groups, and in further embodiments $R^5$ may comprise $C_{16}$ to $C_{18}$ linear or branched saturated alkyl groups. In certain embodiments $R^5$ and one of $R^6$, $R^7$, and $R^8$ may be a $C_{14}$-$C_{22}$ alkyl group, and two of $R^6$, $R^7$, and $R^8$ may be a methyl group. In some embodiments, the alkyl or alkenyl quaternary ammonium salt contains at least one, optionally two or three, hydrocarbon chains having from about 8 to about 30 carbon atoms, and methyl groups.

In other embodiments the alkyl or alkenyl quaternary ammonium compound may comprise a salt having formula (IIa):

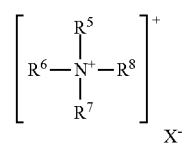

(IIa)

wherein N is nitrogen; $R^5$, $R^6$, $R^7$ and $R^8$ are independently selected from the group consisting of (a) linear or branched, saturated or unsaturated alkyl groups having 1 to 22 carbon atoms, (b) aralkyl groups which are benzyl and substituted benzyl moieties, (c) aryl groups, (d) beta, gamma-unsaturated groups having six or less carbon atoms or hydroxyalkyl groups having two to six carbon atoms, and (e) hydrogen, with the proviso that at least one of the substituents is a linear or branched unsaturated alkyl group; and X is a salt anion.

In some embodiments the alkyl or alkenyl quaternary ammonium salt contains the same or different straight- and/or branched-chain saturated and/or unsaturated alkyl groups of 1 to 22 carbon atoms and complexes. The anion X or counter-ion moiety may be at least one of chloride, methyl sulfate, acetate, iodide, bromide, nitrate, hydroxide, phosphate, methoxysulfate, or mixtures thereof.

The alkyl or alkenyl quaternary ammonium salt may be selected from dimethyl bis[fatty alkyl]ammonium quaternary salt, methyl tris[fatty alkyl]ammonium quaternary salt, dimethyl di($C_{14}$-$C_{18}$ alkyl) ammonium salt, methyl benzyl di($C_{14-18}$ alkyl) ammonium salt, dimethyl benzyl $C_{14}$-$C_{18}$-alkyl ammonium salt, dimethyl $C_{14}$-$C_{18}$-alkyl 2-ethylhexyl ammonium salt, dimethyl bis[hydrogenated tallow]ammonium salt (2M2HT), methyl tris[hydrogenated tallow alkyl] salt (M3HT) distearyldimethyl ammonium salt, methylbenzyl di(hydrogenated tallow) ammonium salt, dimethylbenzyl hydrogenated tallow ammonium salt, trimethyl (C14-C18 alkyl) ammonium salt, trimethyl cocoalkyl ammonium salt, alkyl pyridinium salt, dimethyl benzyl cocoalkyl ammonium salt, oleyl trimethyl ammonium salt, soyaalkyl trimethyl ammonium salt, dialkyl ester of diethanol dimethyl ammonium salt, imidzaoliumquat salt, dialkyl ester of triethanol methyl ammonium salt, trialkyl ester of triethanol methyl ammonium salt, dimethyl hydrogenated tallow-2-ethylhexylammonium salt, trimethyl octadecyl ammonium salt, methyl benzyl dicoco ammonium salt, methyl trihydrogenated tallow ammonium salt, benzyl dimethyl hydrogenated tallow ammonium salt, trimethyl hydrogenated tallow ammonium salt, methyl bis(2-hydroxyethyl[cocoalkyl]) ammonium salt, branched quaternary ammonium salts, trimethyl-alkyl-ammonium salts, and mixtures thereof. The counteranions of the salts may be anions such as chloride, sulfate, carbonate, methylsulfate, bromide, iodide, acetate, nitrate, hydroxide, phosphate, methoxysulfate or mixtures thereof.

The alkyl or alkenyl quaternary ammonium compound may be dimethyl bis[fatty alkyl]ammonium, methyl tris [fatty alkyl]ammonium quaternary salts or mixtures thereof. Illustrative examples of alkyl or alkenyl quaternary ammonium compounds used to make the subject organoclay compositions include but are not limited to dimethyl bis[hydrogenated tallow]ammonium chloride (2M2HT), methyl tris[hydrogenated tallow alkyl] ammonium chloride (M3HT), dimethyl benzyl hydrogenated tallow ammonium chloride and methyl benzyl bis[hydrogenated tallow]ammonium chloride and mixtures comprising one or more of these compounds. In one embodiment, the alkyl or alkenyl quaternary ammonium compound is or comprises dimethyl bis[hydrogenated tallow]ammonium chloride (2M2HT).

In certain embodiments, the organic quaternary ammonium compound may comprise an alkoxylated quaternary ammonium salt having formula (III):

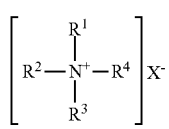

(III)

wherein N is nitrogen; $X^-$ comprises an anion such as at least one of chloride, methyl sulfate, acetate, iodide, bromide, nitrate, hydroxide, phosphate, methoxysulfate or mixtures thereof; $R^1$ comprises a 012 to 030 linear or branched, saturated or unsaturated alkyl or alkenyl group, or alkyl-ester groups having 8 to 30 carbon atoms; $R^2$ comprises H— or a $C_1$ to $C_{30}$ linear or branched, saturated or unsaturated alkyl or alkenyl group; $R^3$ comprises H—, $C_1$ to $C_4$ linear or branched, saturated or unsaturated alkyl or alkenyl group or $R^4$; and, $R^4$ comprises —$(CR^9R^{10}$—$CR^{11}R^{12}O)_y$H, or —$(CR^9R^{10}$—$CR^{11}R^{12}$—$CR^{13}R^{14}O)_y$H, where $R^9$, $R^{10}$, $R^{11}$, $R^{12}$, $R^{13}$ and $R^{14}$ are independently selected from the group consisting of H—, $CH_3$—, and $CH_3CH_2$— and y is 4 to about 20 on average, in other embodiments about 10 to about 20, and in further embodiments 4 to about 15.

In certain embodiments, $R^1$ may comprise $C_{12}$ to $C_{22}$, in other embodiments $C_{14}$-$C_{22}$, and in further embodiments C16 to C18 linear or branched, saturated or unsaturated alkyl or alkenyl group, and in still other embodiments $R^1$ may comprise a $C_{16}$ to $C_{18}$ linear saturated alkyl group. In certain embodiments, $R^2$ may comprise H—, methyl, or a $C_{16}$ to $C_{18}$ linear saturated alkyl group, and in further embodiments a methyl group.

In other embodiments, $R^1$ may comprise a $C_{16}$ to $C_{18}$ linear saturated alkyl group; $R^2$ may comprise a methyl group; $R^3$ and $R^4$ are $(CR^9R^{10}$—$CR^{11}R^{12}O)_y$H where $R^9$, $R^{10}$, $R^{11}$, and $R^{12}$ are independently selected from the group consisting of H—, $CH_3$—, and $CH_3CH_2$—; and y is 4 to 15 on average. In one such embodiment, $R^9$, $R^{10}$, $R^{11}$ and $R^{12}$ are H and y is on average about 7.5.

Illustrative examples of suitable alkoxylated quaternary ammonium salt compounds include, for example, at least one of methyl bis(polyoxyethylene [15])cocoalkyl quaternary ammonium salt, methyl bis(polyoxyethylene [15])oleyl quaternary ammonium salt, and methyl bis(polyoxyethylene [15])octadecyl quaternary ammonium salt, wherein the numbers in brackets refer to the total number of ethylene oxide units. In certain embodiments, the salts are chlorides. In one embodiment, the alkoxylated quaternary ammonium salt is octadecylmethyl [polyoxyethylene (15)] quaternary ammonium chloride.

In other embodiments, the organic quaternary ammonium compound comprises an alkoxylated quaternary ammonium salt having formula (IIIa):

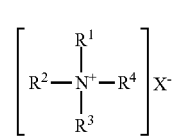

(IIIa)

wherein N is nitrogen; $R^1$ and $R^2$ are alike or different, and are selected from the group consisting of $C_1$-$C_8$ alkyl, benzyl and 2-hydroxyethyl groups; $R^3$ is a $C_1$-$C_8$ alkyl, benzyl or 2-hydroxyethyl group, or an alkoxylated chain containing 0-10 moles of an ethylene oxide moiety and 3-15 moles of an alkylene oxide moiety selected from the group consisting of propylene oxide, butylene oxide and mixtures thereof; and $R^4$ is an alkoxylated chain containing 0-10 moles of an ethylene oxide moiety and 3-15 moles of an alkylene oxide moiety selected from the group consisting of propylene oxide, butylene oxide and mixtures thereof; and X is a salt anion such as at least one of chloride, methyl sulfate, acetate, iodide, bromide, nitrate, hydroxide, phosphate, methoxysulfate or mixtures thereof.

In one embodiment, the alkoxylated quaternary ammonium compound is octyldecylmethyl (polyoxyethylene [15]) quaternary ammonium chloride (C18EO15) and the alkyl or alkenyl quaternary ammonium compound is dimethyl bis [hydrogenated tallow]ammonium chloride (2M2HT).

Although the alkoxylated quaternary ammonium salts may contain alkyl or alkenyl groups, when referred to herein, the "alkyl or alkenyl quaternary ammonium salts" are not alkoxylated quaternary ammonium salts.

The raw materials used to make the quaternary ammonium compounds can be derived from natural oils such as tallow, soya, coconut and palm oil. Useful aliphatic groups in the above formula may be derived from other naturally occurring oils including various vegetable oils, such as corn oil, coconut oil, soybean oil, cottonseed oil, castor oil and the like, as well as various animal oils or fats. The aliphatic groups may likewise be petrochemically derived from, for example, alpha olefins. Representative examples of useful branched, saturated radicals included 12-methylstearyl and 12-ethylstearyl. In certain embodiments, an amine precursor with similar functionalities can be used by converting it to the quaternary compound in-situ, before or after adding the amine to the clay.

In certain embodiments, the phosphonium cation may have the structure $R^1P^+(R^2)_3$ wherein $R^1$ is a $C_8$ to $C_{24}$ alkyl or arylalkyl group and each $R^2$, which may be the same or different, is an aryl, arylalkyl, or a $C_1$ to $C_6$ alkyl group. One $R^2$ may include an alkenyl, alkinyl or monosubstituted derivative thereof. The counter-ion, or anion may be derived from a protic acid, and such anions may be, for purposes of illustration but not limitation, chloride, bromide, iodide, sulfate, methoxysulfate, sulfonate, phosphate, phosphonate, phosphite, or carboxylate, such as acetate. The phosphonium cation may be derived from a phosphine.

In certain embodiments, the amount of the organic cation providing quaternary ammonium compound reacted with the clay may be calculated as an approximate percentage of the cationic exchange capacity of the base phyllosilicate clay mineral. For example, the milliequivalent amount of the quaternary ammonium compound(s) reacted with 100 grams clay (known as the milliequivalent ratio or MER) divided by the cation exchange capacity (CEC) of the clay sample and multiplied by 100 may be expressed as the MER percent of the CEC. The cation exchange capacity (CEC) of the clay can be determined using standard analytical techniques which are known in the art. In one embodiment, the CEC can be determined using methylene blue, i.e. the CEC is equal to the methylene blue exchange capacity. A suitable method for determination of the methylene blue exchange capacity is described in U.S. Pat. No. 9,637,614 B, col. 22, l. 14 to col. 23, l. 25.

In certain embodiments the total amount of organic cation added is 75%-230% of the CEC of the base minerals (mineral clay or clay mixture).

In certain embodiments blends of different organic cations are added in a total amount 75%-230% of the CEC of the base minerals.

In certain embodiments blends of different organic cations are added in a total amount 75%-230% of the CEC of the base minerals whereas each individual organic cationic compound can be added in an amount of 75%-230% of the CEC with the remainder of the organic compounds adding up to a maximum of 230% of the CEC of the base minerals.

In certain embodiments, the amount of cationic quaternary ammonium compound(s) may be about 80 to about 160% of the CEC for the alkyl or alkenyl quaternary ammonium salt and about 0 to about 70% of the CEC for the alkoxylated quaternary ammonium salt. In other embodiments, the amount of cationic quaternary ammonium compound(s) may be about 100 to about 150% of the CEC for the alkyl or alkenyl quaternary ammonium salt and about 13 to about 62% of the CEC for the alkoxylated quaternary ammonium salt. In some embodiments, the amount of cationic quaternary ammonium compound(s) may be about 110 to about 140% of the CEC for the alkyl or alkenyl quaternary ammonium salt and about 19 to about 53% of the CEC for the alkoxylated quaternary ammonium salt.

In certain embodiments, the mineral clay or clay mixture is treated with about 15 to about 160 milliequivalents of the organic quaternary ammonium salt per 100 g of the mineral clay or clay mixture, in other embodiments, about 40 to about 140 milliequivalents, and in still other embodiments, about 70 to about 120 milliequivalents.

In certain embodiments, if the main mineral component is a hormite clay such as Sepiolite, Palygorskite or Attapulgite, about 15 to 100 milliequivalents of the quaternary ammonium salt per 100 g are added. If the main mineral component is a smectite clay such as hectorite, montmorillonite, bentonite, about 50 to 150 milliequivalents of the quaternary ammonium salt per 100 g are added.

The amount of the organic quaternary ammonium compound added to the clay(s) should be sufficient to provide the clay(s) with the characteristics desired. Such characteristics include stability at elevated temperatures and the processability of the organoclay.

Compounds useful for the alkyl or alkenyl, (including aryl groups), quaternary ammonium compounds and/or the alkoxylated quaternary ammonium compounds and/or amine compounds with similar functionalities are manufactured by companies such as Akzo Nobel, CECA (a subsidiary of the Arkema group), Evonik, Solvay, Stepan Company and KAO Chemical Company of Japan. Also, useful commercial products are pre-mixed organic cation fluids containing a blend of two or more quaternary ammonium compounds.

Additionally, the preparation of the organic salts can be achieved by techniques well-known in the art.

Also provided is a drilling fluid comprising a hydrocarbon-based or invert emulsion drilling fluid based composition, and the subject organoclay composition described above. In certain embodiments, the drilling fluid comprises an oil based or invert emulsion drilling fluid base composition, in which the continuous phase is hydrocarbon-based. The base fluid may comprise at least one of diesel oil, mineral oil, mineral seal oil, kerosene, fuel oil, white oil, crude oil, synthetic oil, natural oil, alpha olefins, poly alpha olefins, linear alpha olefins, internal olefins, linear paraffins, linear alkyl benzene and biodegradable oils.

The base fluid (continuous phase) of the drilling fluid may be derived from petroleum, for example, diesel oil, mineral seal oil, kerosene, fuel oil, white oil, crude oil, and the like. Specific examples include number 2 diesel oil and mineral oil. The base fluid may also be derived synthetically, for example, olefins (e.g., alpha or internal) or fluids derived from gas-to-liquid methods, such as the Fischer-Tropsch process. The base fluid may further include natural oils, such as vegetable oil, canola oil, palm oil, or coconut oil. Combinations of more than one of any of these base fluids may also be used in order to meet certain technical and/or environmental specifications.

Where utilized in drilling fluids, the oil vehicle utilized with the subject organoclays may be one which is environmentally benign, by which is meant that the oil is one that over a reasonable course of time will biodegrade in the ground into relatively harmless products.

Oils of this type are well known for use in drilling fluids and similar applications, and are commonly a hydrotreated light distillate. The resultant product contains minimal, if any quantities of aromatic components, and mostly short chain hydrocarbons. The LVT® oil of Calumet Penrico, LLC, and the Low Toxicity Drilling Mud Oil of ExxonMobil, such as those based on ESCAID™ fluids, are commercial examples of such products. Synthesized biodegradable oils based on alpha or internal olefins or the like are also acceptable for the present use, such as AMODRILL® olefin fluid by INEOS USA, LLC, as well as ODC® high purity hydrocarbons of Sasol North America, Inc.

If water is used in the drilling fluid, the amount may be small. When water is intentionally included as a component of a drilling fluid, the fluid may be known as an invert emulsion. Oil based invert emulsion drilling fluids are typically formulated with an Oil/Water Ratio (OWR) of about 95/5 to about 40/60, with water as the aqueous internal phase, typically about 75/25 OWR, meaning of the two components 75 volume percent is oil and 25 volume percent is water. The water of the aqueous internal phase may typically be in the form of brine, which provides salt, such as calcium chloride, for osmotic shale stability.

The properties and composition(s) of drilling fluids may be complex and variable, based upon the required and/or desired properties, and results to be achieved. Some of the most important requirements of drilling fluids are that they be thermally stable and provide adequate rheology control under drilling conditions. These properties can be controlled, at least in part, by including the subject organoclays in the drilling fluid.

Organoclays may impart one or more of the following properties on drilling fluids, including but not limited to thickening, gelling, suspension, wellbore-cleaning, and the like.

The subject organoclay composition(s) (organoclay rheological additives), at least in part, regulate viscosity and anti-settling properties to non-aqueous systems, such as drilling fluids. Incorporation of organoclays into the drilling fluid imparts shear thinning properties to the drilling fluid, in that the drilling fluids will exhibit lower viscosities at higher shear rates.

Organoclays also impart gel strength to the drilling fluid, in that the drilling fluid will behave similarly to a gel at low or zero shear forces, which allows the drilling fluid to suspend drill cuttings and/or weighting agents (described below) under static conditions. Static conditions occur when the drilling fluid is not being pumped in order to allow for other drilling or rig operations to be performed, such as making a connection to the drill shaft or pipe, or changing tools. Organoclays influence the yield point of a drilling fluid, which is the amount of stress (force) necessary to cause the fluid to begin to flow.

The drilling fluid may contain, in certain embodiments, from about 2.85 to about 85.59 kg/m$^3$ (1 to about 30 pounds per barrel) ("ppb" or "lb/bbl"), in other embodiments from about 2.85 to about 42.80 kg/m$^3$ (about 1 to about 15 lb/barrel), in some embodiments about 8.56 to about 28.53 kg/m$^3$ (about 3 to about 10 lb/barrel), and in other embodiments about 8.56 to about 22.82 kg/m$^3$ (about 3 to about 8 lb/barrel), of the subject organoclay composition described herein, taking into account the particular formulation, including mud weight, oil water ratio, type of fluid and the like. As used herein the term "barrel" refers to that volume which is standard in oil field practice and contains 42 U.S. gallons. In certain embodiments, the organoclay(s) is added to the drilling fluid in an amount effective to achieve a yield point of about 0.391 to about 1.709 kg/m$^2$ (8 to about 35 pounds per 100 square feet). The degree of viscosity regulation, suspension or hole cleaning required or desired will have an impact on the clay concentration, as is well known to those skilled in the art.

The drilling fluids may also contain a number of conventional additives typically used in the oil-based or invert emulsion drilling fluid, to provide particular desired application properties.

Drilling fluids for drilling gas or oil wells relevant to the present subject matter may comprise some or all of the following: a base fluid as discussed above; at least one thixotropic agent, such as the subject organoclay composition; water and/or brine; at least one emulsifier; optionally at least one wetting agent; optionally at least one material which imparts alkalinity in the drilling fluid; optionally at least one weighting material; and/or at least one additive, such as rheology modifiers.

In certain embodiments, the drilling fluid comprises, in addition to the subject organoclay composition, at least one of an emulsifier, optionally a primary and a secondary emulsifier, a wetting agent, an acid gas scavenger, a weighting agent, a fluid loss control additive, a bridging agent, an alkalinity control agent, a material that imparts alkalinity, a non-clay rheological additive, and/or a corrosion inhibitor.

Water soluble salts may be added to the drilling fluid, and may include brine salts, including at least one halide of alkali or alkaline earth metals, such as sodium chloride, potassium chloride, sodium bromide, calcium chloride, and the like, optionally in a water solution. Formation brines and seawater may also be used. Salts may be added to control the osmotic pressure of the formulations as needed, according to drilling conditions. Alternatively or additionally, other hygroscopic materials, such as glycols, glycerols and the like, may be used in an aqueous solution similarly to the water soluble salts.

Emulsifiers or emulsifier systems (such as primary and secondary emulsifiers) may form or stabilize the invert emulsion, and/or may additionally serve as wetting agents for solids. Surfactants may be used in the drilling fluids, both for emulsifying the aqueous phase and as wetting agents for the solid phase(s), and may include alkali and alkaline earth metal salts of fatty acids, fatty acid derivatives, rosin acids, tall oil acids, or synthetic emulsifiers such as alkyl aromatic sulfonates, aromatic alkyl sulfonates, long chain sulfates, oxidized tall oils, carboxylated 2-alkyl imidazolines, imidazoline salts, amido amines, amide-imidoamines, alkoxy phenols, polyalkoxy alcohols, alkyl phenols, ether carboxylates, lecithins, high molecular weight alcohols, polymer surfactants and the like.

Weighting agents balance or adjust drilling fluid density/hydrostatic pressure, such as downhole pressure, to prevent fluids from entering the wellbore from the geological formation. These may include materials such as calcium carbonate, silicates, clays, barites, specular hematite, iron ores, siderite, ilmenite, galena, and the like. In certain embodiments, the weighting material may be micronized to improve flow properties and/or reduce sag.

Other additives may be included, such as fluid loss-prevention additives and bridging agents. An acid gas scavenger, such as lime ($Ca(OH)_2$) is often added to the drilling fluid, and may react with some emulsifiers or with gases such as $H_2S$ during drilling.

In certain embodiments, the drilling fluid may contain at least one material which imparts alkalinity to the fluid, such as at least one of alkaline carbonates, alkaline oxides, or alkaline hydroxides, optionally wherein the at least one material which imparts alkalinity comprises lime. In certain embodiments, the at least one material which imparts alkalinity may be present in the drilling fluid in an amount of at least about 0.71 kg/m$^3$ (about 0.25 lb/bbl), optionally from about 0.71 to about 28.53 kg/m$^3$ (about 0.25 to about 10 lb/bbl), or further optionally from about 5.71 kg/m$^3$ to about 28.53 kg/m$^3$ (about 2 to about 10 lb/bbl).

In certain embodiments, invert emulsion drilling fluids may be formed by mixing the desired individual components to make up the drilling fluid. Surfactants, such as the primary and secondary emulsifiers and wetting agents are added to the base oil continuous phase with moderate agitation. The water phase, such as a brine, is added to the base oil/surfactant mixture together with alkalinity control agents and acid gas scavengers. The rheological additives, fluid loss control materials, weighting agents and corrosion inhibition chemicals are also added, with sufficient mixing to ensure homogeneous dispersion of the ingredients in the fluid. The subject organoclay rheology additive may be pre-blended with other ingredients before addition to the base fluid, or it may be added by itself. In certain embodiments, the organoclay is added to the base fluid first, then emulsifiers, then brine, and then other additives.

Additional Uses of Subject Organoclays

The subject organoclay compositions may be used as a thixotrope in non-aqueous liquid compositions, such as organic grease compositions, lubricants, metal working fluids, inks, oil/solvent-based paint formulations, coating, sealant and adhesive materials, unsaturated polyester resin systems, unsaturated polyester/styrene resin systems, vinyl ester systems, acrylic resins, epoxy resin systems, polyurethane resin systems, nanocomposites, mastergels, moulding compounds, cosmetics, cleaners, personal care formulations and home care formulations, among others.

The subject organoclay compositions may be used in a wide variety of liquid organic compositions, containing the organoclay and at least one further chemical component. "A liquid composition" in the present context is a composition which is in a liquid state at the temperature at which it is used and supplemented with the subject organoclay. Typically the liquid organic compositions are liquid at temperatures below 40° C., in many embodiments they are liquid at 25° C. A "liquid organic composition" is a liquid composition containing the subject organoclay and at least one further organic chemical component. Such organic entities can e.g. be compounds or polymers, or mixtures thereof and with each other. Beside non-soluble ingredients, as e.g. fillers and pigments which may also be contained in the liquid organic compositions, the organic components which differ from the subject organoclay may be contained in an amount of at least 50 wt. %, optionally in an amount of 60 wt. % and further optionally in an amount of 70 wt. % or more.

Examples of liquid organic compositions include but are not limited to, in addition to oil drilling fluids and gas drilling fluids, other oil and gas field fluids, such as greases or fracturing fluids; lubricants, metal working fluids, inks; paints, coating materials, sealants, adhesives; composite materials like nanocomposites; and moulding compounds; or simply a liquid organic composition which contains besides the organoclay, only one or more organic solvents.

Such liquid organic compositions contain the subject organoclay composition, typically in an amount from 0.1 to 10 wt. %, optionally 0.1 to 8 wt. % and further optionally 0.5 to 5 wt. %, based on the total weight of the liquid organic composition.

In one embodiment, a hydrophilic polymer slurry in a nonaqueous fluid is provided, comprising the subject organoclay composition, optionally wherein the organoclay composition comprises about 0.1 to about 10% by weight of the slurry, optionally about 0.2 to about 4% by weight.

In certain embodiments, the subject organoclay may be incorporated into compositions comprising at least one unsaturated polyester, such as e.g. coatings, adhesives, sealants, moulding compounds and composite materials. Such unsaturated polyester compositions may contain ethylenically unsaturated monomers.

The term "unsaturated polyester" is used consistent with understanding of the person skilled in the art of unsaturated polyesters (UP) and unsaturated polyester resins (UP resins). Accordingly the term "unsaturated polyester resin" is understood as being a reaction resin comprising polyesters, where at least one of the components forming the polyester, i.e. typically a multivalent alcohol and a multivalent carboxylic acid and/or diol, is ethylenically unsaturated and is copolymerizable with monomeric polymerizable compounds. In other words, the "unsaturated polyesters" contain one or more ethylenically unsaturated carbon-carbon double bonds which are apt to react with ethylenically unsaturated monomers. The at least one unsaturated polyester may be blended with at least one ethylenically unsaturated monomer serving as crosslinking agent. The curing reaction is the copolymerization of the at least one ethylenically unsaturated monomer with the double bonds of the unsaturated polyester.

Not only are unsaturated dicarboxylic acids used in the synthesis of unsaturated polyesters, but also aliphatic or cycloaliphatic dicarboxylic acids and/or aromatic dicarboxylic acids are used to tailor the properties of the crosslinked product, such as phthalic acid and its anhydrides.

Ethylenically unsaturated monomers used with unsaturated polyesters may include those having a vinyl group, allyl group, acrylate group, methacrylate group or a carbon-carbon double bond in a non-terminal region of the monomer. Such ethylenically unsaturated monomers may be selected from the group of styrene, alpha-methylstyrene, methyl acrylate, methyl methacrylate, vinyl acetate, divinyl benzene, diallyl phthalate, triallylcyanurate, and triallyl phosphate.

The subject organoclays may be used in coating, adhesive or sealant compositions in an amount such that the final composition will have a flow curve which allows application but prevents drainage from or sag of the material from the surface to which the ready to use formulations are applied.

In certain embodiments, the subject organoclays can be stirred and dispersed directly in an epoxy resin solution, and will provide highly satisfactory gelling properties. Commonly used epoxy resins are formed by reacting reactive phenols, alcohols, acids and/or amines with epichlorohydrin. The number of reactive base entities, which form epoxy resins by reaction of epichlorohydrin is almost unlimited, resulting in a large number of technically important resins. Commonly, an oxirane ring is present in the epoxy resins in form of a glycidyl group. Unsaturated aliphatic and cycloaliphatic compounds may be epoxidized with e.g. peracetic acid.

The subject organoclays may also be used in preparing nanocomposites, by conventional methods, and with a large variety of polymerizable polymers such as polyamides, epoxy resins, polyvinyl resins, polyacrylamides, and the like. When used in composites such as nanocomposites, the subject organoclays yield unexpected improvements in the mechanical and other properties of the composite, including with respect to tensile strength, tensile modulus and flex modulus, all of which are highly significant attributes.

Although the embodiments have been described in detail through the above detailed description and the preceding examples, these examples are for the purpose of illustration only and it is understood that variations and modifications can be made by one skilled in the art without departing from the spirit and the scope of the invention. It should be understood that the embodiments described above are not only in the alternative, but can be combined.

The following examples are set forth merely to further illustrate the subject organoclays, particularly as used as the primary viscosifier for an oil-based drilling fluid, and as the suspension aid in a solvent based polymer suspension, which is used in hydraulic fracturing fluids. The illustrative examples should not be construed as limiting the subject matter in any manner.

EXAMPLES

Preparation of Organoclay A.

Samples of Organoclay A (A-1 through A-14) were made using standard organoclay preparation techniques well-known in the art with an organic (alkyl) quaternary ammonium salt and Synergist Solution A. The comparative sample (A-15) did not include the synergist. First, the calculated amount of refined, MG sheared smectite (montmorillonite) slurry was weighed and added to the mixing vessel to achieve 60 grams of smectite on a dry clay weight basis, and mixing began while bringing the mixture to temperature (about 60-65° C.). Then, a synergist was added in the amounts (including carrier/solvent) indicated in Tables 2-5 and 7-10 for each run sample, while continuing to mix for 2-3 minutes. Then the organic quaternary ammonium (NH4+) compound was added based on the amount indicated in Tables 2-5 and 7-10 for each run sample, allowing 30-45 minutes for reaction while mixing and scraping the sides of the vessel at least 3 times during mixing. Next, samples were filtered and placed in a blower oven overnight at 62.5° C. Finally, the samples were milled in a Retsch mill using a 0.2 screen and allowed to rehydrate overnight before testing.

In practice, the organic quaternary ammonium compound may be added to the clay slurry before or after the synergist (powder or solution) is added, or they may be added simultaneously or as a mixture. The organic quaternary ammonium compound used to treat the clay in the examples was a conventional alkyl quaternary ammonium salt, dimethyl dihydrogenated tallow ammonium chloride (2M2HT).

Synergist Solution A was comprised of about 60 weight percent of the subject synergist (as defined in the appended claims) in a solution with propylene glycol as a carrier/solvent. The synergist comprised an amine salt of trimer acid having in the range of about 42 to about 60 carbon atoms, and an amine salt of a tall oil fatty (monocarboxylic) acid, wherein the amines comprised an unsaturated monoamine having from about 10 to about 24 carbon atoms. The results from these examples showed that the Synergist Solution A type modified organoclay product had a significant effect on the low shear viscosity on the two oil based muds used for testing, while having a minimal effect on the high shear viscosity.

Testing

Each organoclay sample identified in the Examples and Comparative Example (collectively referred to as "samples") was used to prepare the oil-based mud (OBM) drilling fluids described below. These OBMs were prepared and tested as described herein and according to API RP 13B-2, "Recommended Practice for Field Testing of Oil-based Drilling Fluids", Fifth Edition, which is incorporated herein by reference. After mixing the OBMs, each Example and Comparative Example (initially and after aging at 65.5° C. and 121.1° C. [150° F. and 250° F.]) were placed in a Thermo cup of a Model 900 Viscometer ("Viscometer") from OH Testing Equipment, Inc., and run at 600 rpm until the target temperature of 48.9° C. (120° F.) was reached, after which the rheology characteristics were measured using the Viscometer at 600, 300, 200, 100, 6 and 3 rpm, in order to obtain a rheology profile of each sample. It is noted that the Viscometer's output is in "dial readings" at a given rpm, which may be converted to centipoise, but the industry standard is to merely utilize the dial readings for simplicity.

The plastic viscosity ("PV") of each sample was then calculated by subtracting the measurement at 300 rpm from the measurement at 600 rpm. The yield point ("YP") of each sample was also calculated, by subtracting the PV from the measurement at 300 rpm. The gel strength ("GS") is the maximum deflection (dial reading) taken at 3 rpm after a period of rest. Gel strengths were measured for each sample after 10 seconds and 10 minutes of rest. Electrical stability ("ES") of each sample was also measured using a FANN® 32E electrical stability tester (available from the Fann Instrument Company, Houston, Tex.) which measures how much current (in volts) is required to create an arc in the drilling fluid sample. A higher number indicates greater emulsion stability of the drilling fluid.

Organoclays A-1 through A-14, and comparative organoclay A-15 were tested in Drilling Fluid #1 according to the composition and mixing times described in Table 1. The organoclays used for the comparative examples were made with no synergist added. The exemplified oil based muds were prepared, for the convenience of testing at multiple aging temperatures, in larger batches of 420 ml volume. The values for standard 350 ml ("lab barrel") units are included for reference.

TABLE 1

| | Drilling Fluid #1 | | |
|---|---|---|---|
| Material | Amount (grams per 350 ml) | Amount (grams per 420 ml) | Mixing time (Minutes) |
| Diesel #2 | 183 | 220 | n/a |
| Organoclay A | 5 | 6.6 | 5 |
| Lime | 3 | 3.6 | 5 |
| Emulsifier | 4 | 4.8 | 5 |
| 25% CaCl$_2$ brine | 97 | 116 | 20 |
| Barite | 150 | 180 | 5 |
| OCMA clay* | 20 | 24 | 5 |

*The OCMA clay was added to simulate drill solids.

After mixing all the components on the overhead mixer (Table 1), the samples were then sheared for 5-minutes on a Silverson mixer at 6,000 rpm to stabilize the emulsion. In order to test the viscosities of the various OBM samples, after mixing the desired sample in a Silverson mixer the sample was transferred to a Thermo cup and placed on the OFITE 900 viscometer (a direct-indicating viscometer) and heated to 48.9° C. (120° F.). While heating, the viscometer was mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes was measured.

PV and YP were then calculated as follows:

PV=600 reading−300 reading

YP=300 reading−PV

ES values are electrical stability measurements taken using an Electrical Stability Meter (also known as an emulsion stability tester). ES values were measured immediately following the viscosity measurements of each sample.

Table 2 lists the results of initial viscosity testing as described above for the various organoclay A samples tested in Drilling Fluid #1.

TABLE 2

Initial Drilling Fluid #1 Results

| | Organoclay A | | | | | | | | | | | | |
|---|---|---|---|---|---|---|---|---|---|---|---|---|---|
| | % Synergist | MER Quaternary | Dial Reading at Listed rpm | | | | | | | | | GS | |
| Ex. # | Solution | NR4+ | 600 | 300 | 200 | 100 | 6 | 3 | PV | YP | 10" | 10' | ES |
| A-1 | 15 | 100 | 80 | 53 | 41 | 30 | 16 | 15 | 27 | 26 | 16 | 20 | 490 |
| A-2 | 15 | 90 | 81 | 54 | 41 | 30 | 16 | 15 | 27 | 26 | 15 | 19 | 413 |
| A-3 | 10 | 95 | 71 | 46 | 36 | 24 | 11 | 10 | 25 | 21 | 11 | 14 | 380 |
| A-4 | 5 | 100 | 71 | 45 | 34 | 24 | 11 | 10 | 26 | 20 | 10 | 12 | 396 |
| A-5 | 10 | 95 | 79 | 52 | 40 | 28 | 14 | 13 | 27 | 25 | 13 | 16 | 461 |
| A-6 | 5 | 90 | 78 | 48 | 35 | 24 | 10 | 9 | 30 | 19 | 9 | 11 | 321 |
| A-7 | 10 | 95 | 73 | 49 | 38 | 27 | 14 | 14 | 24 | 25 | 14 | 18 | 418 |
| A-8 | 2.9 | 95 | 68 | 45 | 34 | 23 | 9 | 8 | 23 | 22 | 7 | 8 | 276 |
| A-9 | 10 | 95 | 79 | 52 | 39 | 27 | 12 | 11 | 27 | 25 | 11 | 14 | 392 |
| A-10 | 17.1 | 95 | 83 | 54 | 41 | 29 | 14 | 13 | 30 | 24 | 13 | 17 | 446 |
| A-11 | 10 | 87.9 | 73 | 47 | 35 | 24 | 12 | 11 | 26 | 21 | 12 | 15 | 365 |
| A-12 | 10 | 95 | 78 | 50 | 38 | 26 | 12 | 12 | 28 | 23 | 11 | 14 | 372 |
| A-13 | 10 | 102.1 | 72 | 49 | 39 | 28 | 14 | 13 | 24 | 25 | 13 | 16 | 480 |
| A-14 | 10 | 95 | 71 | 46 | 34 | 24 | 10 | 9 | 26 | 20 | 9 | 12 | 324 |
| A-15 Comparative | 0 | 95 | 63 | 39 | 28 | 19 | 7 | 6 | 25 | 14 | 6 | 7 | 286 |

Samples A-3, A-5, A-7, A-12, and A-14 were separate organoclay repeats made with the same amount of quaternary ammonium salt and synergist A treatment. Relative to the comparative sample, A-15, every synergist-treated sample had higher initial testing values than the control in 6 rpm and initial yield point. The same can be said of the gel strength (GS) values, at 10 seconds and 10 minutes. These results show the 6 rpm and GS values increase as the amount of synergist increases. The changes in the MER values for the quaternary ammonium (NH4+) compound had minimal impact on the properties of the drilling fluid containing Organoclay A. The synergist modification of the organoclay provided higher low shear without a significant increase in high shear, as was desired.

In order to obtain the AHR-150 and AHR-250 heat-aged samples, the OBM samples were returned to a mixing vessel, mixed for 5 minutes with an overhead mixer, and then transferred into separate aging cells. For 121.1° C. (250° F.) hot rolling condition (AHR-250), the samples were placed in an appropriate aging cell; and 20.7 bar (300 psi) Nitrogen pressure was applied (apply 3×; release after first two charges and hold after third) on the aging cells to prevent volatilization of water in oil based mud. Then, the samples were hot rolled at either 65.5° C. (150° F.) (AHR-150) or 121.1° C. (250° F.) (AHR-250), respectively, for 16 hours.

After removal of the samples following the hot rolling, the cells were air cooled and then vented to release any pressure from the cell as appropriate. The samples were mixed for five minutes on an overhead mixer. Then the OBM samples were transferred into the Thermo cup, placed on the OFITE 900 viscometer, and heated to 48.9° C. (120° F.) while mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes were measured. The PV, YP, and ES were measured or calculated as described above.

Table 3 lists the results of AHR-150 viscosity testing as described above for the various organoclay A samples tested in Drilling Fluid #1.

TABLE 3

Drilling Fluid #1 Results AHR-150

| | Organoclay A | | | | | | | | | | | | |
|---|---|---|---|---|---|---|---|---|---|---|---|---|---|
| | % Synergist | MER Quaternary | Dial Reading at Listed rpm | | | | | | | | | GS | |
| Ex. # | Solution | NR4+ | 600 | 300 | 200 | 100 | 6 | 3 | PV | YP | 10" | 10' | ES |
| A-1 | 15 | 100 | 86 | 55 | 42 | 29 | 15 | 14 | 31 | 25 | 15 | 23 | 524 |
| A-2 | 15 | 90 | 86 | 53 | 39 | 27 | 13 | 13 | 33 | 20 | 13 | 21 | 440 |
| A-3 | 10 | 95 | 85 | 53 | 40 | 27 | 13 | 12 | 32 | 21 | 13 | 17 | 444 |
| A-4 | 5 | 100 | 83 | 53 | 39 | 26 | 12 | 11 | 30 | 23 | 11 | 14 | 459 |
| A-5 | 10 | 95 | 80 | 53 | 40 | 28 | 13 | 13 | 27 | 26 | 13 | 19 | 510 |
| A-6 | 5 | 90 | 76 | 48 | 36 | 24 | 10 | 10 | 28 | 20 | 10 | 12 | 391 |
| A-7 | 10 | 95 | 77 | 51 | 39 | 27 | 13 | 13 | 26 | 25 | 13 | 18 | 474 |
| A-8 | 2.9 | 95 | 66 | 40 | 31 | 20 | 7 | 7 | 26 | 14 | 7 | 8 | 328 |
| A-9 | 10 | 95 | 88 | 56 | 41 | 28 | 13 | 12 | 33 | 23 | 12 | 17 | 414 |
| A-10 | 17.1 | 95 | 92 | 55 | 40 | 28 | 13 | 13 | 37 | 19 | 14 | 23 | 477 |
| A-11 | 10 | 87.9 | 75 | 46 | 33 | 22 | 9 | 8 | 29 | 17 | 9 | 13 | 394 |
| A-12 | 10 | 95 | 83 | 51 | 37 | 25 | 12 | 11 | 31 | 20 | 11 | 16 | 430 |
| A-13 | 10 | 102.1 | 79 | 52 | 40 | 28 | 13 | 13 | 27 | 25 | 13 | 19 | 505 |
| A-14 | 10 | 95 | 71 | 44 | 33 | 21 | 9 | 9 | 27 | 17 | 9 | 13 | 366 |
| A-15 Comparative | 0 | 95 | 67 | 40 | 31 | 20 | 7 | 6 | 27 | 14 | 6 | 7 | 359 |

Table 4 lists the results of AHR-250 viscosity testing as described above for the various organoclay A samples tested in Drilling Fluid #1.

TABLE 4

Drilling Fluid #1 Results AHR-250

| | Organoclay A | | | | | | | | | | | | |
|---|---|---|---|---|---|---|---|---|---|---|---|---|---|
| | % Synergist | MER Quaternary | Dial Reading at Listed rpm | | | | | | | | GS | | |
| Ex. # | Solution | NR4+ | 600 | 300 | 200 | 100 | 6 | 3 | PV | YP | 10" | 10' | ES |
| A-1 | 15 | 100 | 77 | 51 | 39 | 28 | 14 | 14 | 26 | 25 | 14 | 19 | 507 |
| A-2 | 15 | 90 | 76 | 49 | 38 | 26 | 14 | 13 | 27 | 22 | 13 | 18 | 460 |
| A-3 | 10 | 95 | 73 | 49 | 37 | 26 | 13 | 12 | 25 | 24 | 12 | 15 | 440 |
| A-4 | 5 | 100 | 74 | 47 | 36 | 25 | 12 | 11 | 26 | 21 | 11 | 12 | 433 |
| A-5 | 10 | 95 | 82 | 53 | 39 | 28 | 14 | 13 | 29 | 25 | 13 | 16 | 487 |
| A-6 | 5 | 90 | 70 | 44 | 34 | 23 | 10 | 9 | 26 | 18 | 9 | 10 | 346 |
| A-7 | 10 | 95 | 81 | 53 | 39 | 27 | 13 | 13 | 28 | 24 | 12 | 15 | 442 |
| A-8 | 2.9 | 95 | 64 | 39 | 30 | 20 | 8 | 8 | 26 | 13 | 7 | 8 | 373 |
| A-9 | 10 | 95 | 73 | 47 | 37 | 26 | 13 | 12 | 26 | 21 | 11 | 14 | 432 |
| A-10 | 17.1 | 95 | 71 | 45 | 36 | 26 | 13 | 13 | 26 | 19 | 13 | 19 | 465 |
| A-11 | 10 | 87.9 | 64 | 39 | 30 | 21 | 9 | 9 | 25 | 14 | 9 | 11 | 343 |
| A-12 | 10 | 95 | 66 | 42 | 33 | 24 | 11 | 11 | 25 | 17 | 11 | 13 | 403 |
| A-13 | 10 | 102.1 | 69 | 44 | 35 | 25 | 12 | 12 | 26 | 18 | 11 | 14 | 474 |
| A-14 | 10 | 95 | 70 | 44 | 34 | 23 | 11 | 10 | 26 | 19 | 9 | 12 | 343 |
| A-15 Comparative | 0 | 95 | 65 | 40 | 30 | 20 | 7 | 6 | 25 | 15 | 6 | 7 | 313 |

There was little change in test results upon aging at 65.5° C. (150° F.), as expected for a wet-processed organoclay. As demonstrated in these Tables, drilling fluid #1, the samples with higher levels of Synergist A had higher low shear values and gel strengths.

To demonstrate greater thermal stability, the samples previously aged at 65.5° C. (150° F.) and 121.1° C. (250° F.), were combined and mixed. These samples were then aged for an additional 16 hours at 148.9° C. (300° F.) and are reported below as the AHR-300 test. After removal of the samples following the hot rolling, the cells were then air cooled before venting to release pressure. The samples were mixed for 5 minutes on an overhead mixer. Then the samples were transferred into the Thermo cup, placed on the OFITE 900 viscometer, and heated to 48.9° C. (120° F.) while mixing at 600 rpm. Once the desired temperature is reached, dial readings were taken at 600 rpm, 300 rpm, 200 rpm, 100 rpm, 6 rpm, and 3 rpm. Then, the GS at 10 seconds and 10 minutes was measured. The PV, YP, and ES were measured or calculated as above.

Table 5 lists the results of AHR-300 viscosity testing as described above for the various organoclay A samples tested in Drilling Fluid #1.

TABLE 5

Drilling Fluid #1 Results AHR-300

| | Organoclay A | | | | | | | | | | | | |
|---|---|---|---|---|---|---|---|---|---|---|---|---|---|
| | % Synergist | MER Quaternary | Dial Reading at Listed rpm | | | | | | | | GS | | |
| Ex. # | Solution | NR4+ | 600 | 300 | 200 | 100 | 6 | 3 | PV | YP | 10" | 10' | ES |
| A-1 | 15 | 100 | 85 | 55 | 42 | 29 | 15 | 14 | 30 | 24 | 14 | 19 | 536 |
| A-2 | 15 | 90 | 76 | 50 | 39 | 27 | 14 | 13 | 26 | 24 | 13 | 20 | 463 |
| A-3 | 10 | 95 | 70 | 45 | 35 | 24 | 12 | 11 | 25 | 20 | 11 | 14 | 427 |
| A-4 | 5 | 100 | 73 | 49 | 36 | 24 | 11 | 11 | 25 | 24 | 10 | 11 | 424 |
| A-5 | 10 | 95 | 75 | 49 | 39 | 27 | 13 | 13 | 26 | 24 | 13 | 16 | 497 |
| A-6 | 5 | 90 | 75 | 47 | 35 | 24 | 10 | 9 | 28 | 20 | 9 | 10 | 358 |
| A-7 | 10 | 95 | 85 | 54 | 39 | 27 | 13 | 12 | 31 | 23 | 12 | 15 | 438 |
| A-8 | 2.9 | 95 | 66 | 40 | 31 | 22 | 9 | 8 | 26 | 14 | 8 | 9 | 340 |
| A-9 | 10 | 95 | 69 | 45 | 36 | 26 | 13 | 13 | 25 | 20 | 13 | 16 | 447 |
| A-10 | 17.1 | 95 | 73 | 47 | 39 | 28 | 15 | 14 | 25 | 22 | 15 | 23 | 496 |
| A-11 | 10 | 87.9 | 66 | 41 | 33 | 23 | 11 | 10 | 25 | 16 | 10 | 14 | 395 |
| A-12 | 10 | 95 | 67 | 43 | 35 | 24 | 12 | 12 | 24 | 20 | 11 | 14 | 432 |
| A-13 | 10 | 102.1 | 72 | 46 | 37 | 26 | 14 | 13 | 25 | 21 | 13 | 16 | 528 |
| A-14 | 10 | 95 | 68 | 44 | 35 | 24 | 12 | 11 | 25 | 19 | 11 | 14 | 367 |
| A-15 Comparative | 0 | 95 | 64 | 39 | 29 | 20 | 8 | 7 | 25 | 14 | 7 | 7 | 341 |

The comparative control sample and organoclays treated with Synergist A show little change after aging at 148.9° C. (300° F.). Organoclays A-1 to A-14 again exhibited higher low shear value (6-rpm readings) relative to the control (A-15) as previously seen.

A comparison of 6 RPM response (Diesel OBM) initially and after hot rolling at 121.1° C. (250° F.) for 16 hours for the organoclay processed at 95 MER alkyl quaternary ammonium compound with and without addition of Synergist A at 10 weight % can be made. The sample without Synergist A has a lower 6 rpm value in this OBM test both initially and AHR-250. Hot rolling at 121.1° C. (250° F.) did not have an effect on these samples, indicating sample/OBM stability at the temperature, and maintenance of the greater low shear advantage for the OBM containing synergist-treated Organoclay A.

the viscometer was mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes was measured. The PV, YP, and ES were measured or calculated as described above.

Table 7 lists the results of initial viscosity testing as described above for the various organoclay A' samples tested in Drilling Fluid #2.

TABLE 7

Initial Drilling Fluid #2 Results

| | Organoclay A' | | | | | | | | | | | | |
|---|---|---|---|---|---|---|---|---|---|---|---|---|---|
| | % Synergist | MER Quaternary | Dial Reading at Listed rpm | | | | | | | | | GS | | |
| Ex. # | Solution | NR4+ | 600 | 300 | 200 | 100 | 6 | 3 | PV | YP | 10" | 10' | ES |
| A'-1 | 15 | 100 | 66 | 41 | 29 | 19 | 9 | 8 | 25 | 16 | 9 | 13 | 300 |
| A'-2 | 15 | 90 | 62 | 39 | 30 | 20 | 9 | 8 | 23 | 15 | 9 | 15 | 269 |
| A'-3 | 10 | 95 | 59 | 35 | 27 | 18 | 7 | 6 | 24 | 12 | 7 | 10 | 323 |
| A'-4 | 5 | 100 | 64 | 37 | 26 | 17 | 6 | 5 | 28 | 9 | 5 | 7 | 278 |
| A'-5 | 10 | 95 | 68 | 41 | 29 | 19 | 7 | 7 | 27 | 14 | 7 | 9 | 270 |
| A'-6 | 5 | 90 | 62 | 37 | 28 | 18 | 7 | 6 | 25 | 12 | 6 | 8 | 261 |
| A'-7 | 10 | 95 | 62 | 37 | 29 | 19 | 7 | 6 | 25 | 13 | 7 | 10 | 278 |
| A'-8 | 2.9 | 95 | 60 | 35 | 25 | 16 | 5 | 4 | 25 | 10 | 4 | 7 | 235 |
| A'-9 | 10 | 95 | 63 | 39 | 30 | 20 | 8 | 7 | 24 | 15 | 7 | 10 | 266 |
| A'-10 | 17.1 | 95 | 62 | 39 | 31 | 21 | 10 | 9 | 23 | 16 | 11 | 16 | 285 |
| A'-11 | 10 | 87.9 | 62 | 37 | 29 | 19 | 8 | 7 | 25 | 13 | 7 | 10 | 263 |
| A'-12 | 10 | 95 | 65 | 40 | 29 | 19 | 8 | 7 | 25 | 15 | 7 | 11 | 263 |
| A'-13 | 10 | 102.1 | 60 | 36 | 28 | 19 | 7 | 6 | 24 | 12 | 7 | 9 | 295 |
| A'-14 | 10 | 95 | 60 | 36 | 28 | 18 | 7 | 6 | 24 | 12 | 7 | 10 | 269 |
| A'-15 Comparative | 0 | 95 | 56 | 31 | 23 | 14 | 4 | 3 | 25 | 7 | 3 | 5 | 255 |

The Organoclay A samples, A-1 through A-15, were tested in Drilling Fluid #2 according to the composition and mixing times described in Table 6. The Organoclay A samples were designated A'-1 through A'-15 to distinguish the test results in this drilling fluid. The organoclay used for the comparative examples was made with no synergist added.

TABLE 6

Drilling Fluid #2

| Material | Amount (grams per 350 ml) | Amount (grams per 420 ml) | Mixing time (Minutes) |
|---|---|---|---|
| LVT-200 | 179 | 215 | n/a |
| Organoclay A' | 7 | 8.4 | 5 |
| Lime | 3 | 3.6 | 5 |
| Emulsifier | 3.8 | 4.6 | 5 |
| 25% CaCl2 brine | 94.5 | 113.6 | 20 |
| Barite | 155.7 | 187.2 | 5 |
| OCMA clay | 20 | 24 | 5 |

The LVT® oils of Calumet Penrico, LLC, are a commercial example of a hydrotreated light distillate for use in drilling fluids and similar applications.

After mixing all the components on the overhead mixer (Table 1), the samples were then sheared for 5-minutes on a Silverson mixer at 6,000 rpm to stabilize the emulsion. In order to test the viscosities of the various organoclay samples, after mixing each OBM sample in a Silverson mixer, the sample was transferred to a Thermo cup and placed on the OFITE 900 viscometer (a direct-indicating viscometer) and heated to 48.9° C. (120° F.). While heating, Again, the Comparative Example A'-15 organoclay was the "control". LVT-200 is a low aromatic mineral oil, and is a much more difficult solvent for the organoclays to "yield in." The addition level of the organoclay for Drilling Fluid 2 was 19.97 kg/m$^3$ (7 lb/bbl) for the mineral oil system as compared to only 14.27 kg/m$^3$ (5 lb/bbl) for the Drilling Fluid #1 diesel system.

As with Drilling Fluid #1, the synergist-treated samples with increasing amounts of synergist, showed increased 6-RPM dial readings, yield point (YP), and gel strength (GS) values as compared to the control. The 600 rpm readings and PV showed little change, as was desired.

In order to obtain the AHR-150 and AHR-250 heat-aged samples, the samples were returned to a mixing vessel, mixed with an overhead mixer, and then transferred into separate aging cells. For 121.1° C. (250° F.) hot rolling (AHR-250), the samples were placed in an appropriate aging cell; and 20.7 bar (300 psi) Nitrogen pressure was applied (apply 3×; release after first two charges and hold after third) on the aging cells to prevent volatilization of water in oil based fluid. Then, the samples were hot rolled at either 65.5° C. (150° F.) (AHR-150) or 121.1° C. (250° F.) (AHR-250), respectively, for 16 hours.

After removal of the samples following the hot rolling, the cells were air cooled and then vented to release any pressure from the cell as appropriate. The samples were mixed for 5 minutes with an overhead mixer. Then the OBM samples were transferred into the Thermo cup, placed on the OFITE 900 viscometer, and heated to 48.9° C. (120° F.) while mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes were measured. The PV, YP, and ES were measured or calculated as above.

Table 8 lists the results of AHR-150 viscosity testing as described above for the various organoclay A' samples tested in Drilling Fluid #2.

TABLE 8

Drilling Fluid #2 Results AHR-150

| | Organoclay A' | | | | | | | | | | | | | |
|---|---|---|---|---|---|---|---|---|---|---|---|---|---|---|
| | % Synergist | MER Quaternary | Dial Reading at Listed rpm | | | | | | | | | GS | | |
| Ex. # | Solution | NR4+ | 600 | 300 | 200 | 100 | 6 | 3 | PV | YP | 10" | 10' | ES |
| A'-1 | 15 | 100 | 67 | 39 | 27 | 17 | 6 | 6 | 28 | 11 | 6 | 11 | 327 |
| A'-2 | 15 | 90 | 67 | 38 | 26 | 16 | 7 | 6 | 29 | 10 | 7 | 14 | 292 |
| A'-3 | 10 | 95 | 59 | 36 | 25 | 16 | 6 | 5 | 24 | 12 | 6 | 10 | 308 |
| A'-4 | 5 | 100 | 60 | 35 | 24 | 15 | 5 | 5 | 25 | 10 | 5 | 7 | 303 |
| A'-5 | 10 | 95 | 55 | 32 | 24 | 16 | 6 | 6 | 23 | 9 | 6 | 10 | 297 |
| A'-6 | 5 | 90 | 61 | 35 | 25 | 16 | 5 | 5 | 26 | 9 | 5 | 7 | 316 |
| A'-7 | 10 | 95 | 67 | 40 | 27 | 17 | 6 | 6 | 27 | 13 | 7 | 11 | 312 |
| A'-8 | 2.9 | 95 | 58 | 33 | 24 | 15 | 5 | 4 | 25 | 8 | 5 | 6 | 278 |
| A'-9 | 10 | 95 | 68 | 39 | 27 | 17 | 6 | 6 | 29 | 11 | 6 | 10 | 292 |
| A'-10 | 17.1 | 95 | 63 | 38 | 28 | 18 | 7 | 7 | 26 | 12 | 8 | 16 | 312 |
| A'-11 | 10 | 87.9 | 58 | 33 | 25 | 15 | 5 | 5 | 25 | 8 | 5 | 9 | 293 |
| A'-12 | 10 | 95 | 59 | 36 | 26 | 16 | 6 | 5 | 24 | 12 | 6 | 10 | 314 |
| A'-13 | 10 | 102.1 | 66 | 37 | 26 | 17 | 6 | 6 | 30 | 7 | 6 | 10 | 330 |
| A'-14 | 10 | 95 | 59 | 35 | 26 | 16 | 6 | 5 | 24 | 12 | 6 | 11 | 305 |
| A'-15 Comparative | 0 | 95 | 60 | 35 | 25 | 15 | 4 | 4 | 25 | 10 | 4 | 4 | 277 |

Table 9 lists the results of AHR-250 viscosity testing as described above for the various organoclay A' samples tested in Drilling Fluid #2.

TABLE 9

Drilling Fluid #2 Results AHR-250

| | Organoclay A' | | | | | | | | | | | | | |
|---|---|---|---|---|---|---|---|---|---|---|---|---|---|---|
| | % Synergist | MER Quaternary | Dial Reading at Listed rpm | | | | | | | | | GS | | |
| Ex. # | Solution | NR4+ | 600 | 300 | 200 | 100 | 6 | 3 | PV | YP | 10" | 10' | ES |
| A'-1 | 15 | 100 | 68 | 40 | 31 | 21 | 9 | 9 | 28 | 13 | 10 | 18 | 305 |
| A'-2 | 15 | 90 | 67 | 40 | 31 | 22 | 10 | 10 | 27 | 13 | 10 | 18 | 329 |
| A'-3 | 10 | 95 | 62 | 37 | 28 | 19 | 8 | 7 | 25 | 12 | 7 | 11 | 306 |
| A'-4 | 5 | 100 | 60 | 36 | 27 | 18 | 7 | 6 | 25 | 11 | 6 | 8 | 313 |
| A'-5 | 10 | 95 | 66 | 42 | 30 | 20 | 8 | 8 | 25 | 17 | 8 | 12 | 325 |
| A'-6 | 5 | 90 | 62 | 36 | 28 | 18 | 7 | 6 | 26 | 10 | 6 | 8 | 272 |
| A'-7 | 10 | 95 | 63 | 37 | 29 | 19 | 8 | 7 | 26 | 12 | 8 | 12 | 315 |
| A'-8 | 2.9 | 95 | 61 | 36 | 27 | 18 | 6 | 5 | 25 | 11 | 5 | 7 | 287 |
| A'-9 | 10 | 95 | 69 | 43 | 32 | 21 | 8 | 8 | 27 | 16 | 8 | 13 | 308 |
| A'-10 | 17.1 | 95 | 66 | 40 | 31 | 22 | 10 | 10 | 26 | 15 | 11 | 20 | 342 |
| A'-11 | 10 | 87.9 | 63 | 37 | 29 | 19 | 8 | 7 | 26 | 12 | 7 | 13 | 316 |
| A'-12 | 10 | 95 | 63 | 37 | 29 | 19 | 8 | 7 | 26 | 12 | 7 | 12 | 299 |
| A'-13 | 10 | 102.1 | 66 | 40 | 30 | 20 | 9 | 8 | 26 | 14 | 8 | 12 | 337 |
| A'-14 | 10 | 95 | 62 | 37 | 29 | 20 | 8 | 7 | 25 | 13 | 7 | 12 | 298 |
| A'-15 Comparative | 0 | 95 | 59 | 33 | 25 | 16 | 5 | 4 | 26 | 8 | 4 | 5 | 269 |

The results show an increase in low shear values and gel strength as the amount of Synergist A is increased. To demonstrate greater thermal stability, the samples previously aged at 65.5° C. (150° F.) and 121.1° (250° F.), were combined and mixed. These samples were then aged for an additional 16 hours at 148.9° C. (300° F.). After removal of the samples following the hot rolling, the cells were then air cooled before venting to release pressure. The samples were mixed for 5 minutes on an overhead mixer. Then the samples were transferred into the Thermo cup, placed on the OFITE 900 viscometer, and heated to 48.9° C. (120° F.) while mixing at 600 rpm. Once the desired temperature is reached, dial readings were taken at 600 rpm, 300 rpm, 200 rpm, 100 rpm, 6 rpm, and 3 rpm. Then, the GS at 10 seconds and 10 minutes was measured. The PV, YP, and ES were measured or calculated as above.

Table 10 lists the results of AHR-300 viscosity testing as described above for the various organoclay A' samples tested in Drilling Fluid #2.

TABLE 10

Drilling Fluid #2 Results AHR-300

| | Organoclay A' | | | | | | | | | | | | |
|---|---|---|---|---|---|---|---|---|---|---|---|---|---|
| | % Synergist | MER Quaternary | Dial Reading at Listed rpm | | | | | | | | | GS | |
| Ex. # | Solution | NR4+ | 600 | 300 | 200 | 100 | 6 | 3 | PV | YP | 10" | 10' | ES |
| A'-1 | 15 | 100 | 65 | 40 | 31 | 22 | 11 | 10 | 25 | 15 | 11 | 21 | 367 |
| A'-2 | 15 | 90 | 66 | 40 | 32 | 23 | 11 | 11 | 26 | 15 | 12 | 22 | 361 |
| A'-3 | 10 | 95 | 65 | 39 | 30 | 21 | 9 | 9 | 26 | 13 | 9 | 14 | 341 |
| A'-4 | 5 | 100 | 66 | 41 | 30 | 19 | 7 | 7 | 26 | 15 | 7 | 8 | 343 |
| A'-5 | 10 | 95 | 67 | 42 | 32 | 21 | 10 | 9 | 25 | 17 | 9 | 14 | 329 |
| A'-6 | 5 | 90 | 65 | 40 | 30 | 19 | 7 | 7 | 25 | 15 | 7 | 9 | 361 |
| A'-7 | 10 | 95 | 63 | 38 | 30 | 21 | 9 | 9 | 25 | 13 | 9 | 13 | 367 |
| A'-8 | 2.9 | 95 | 61 | 36 | 27 | 18 | 6 | 6 | 25 | 11 | 6 | 7 | 313 |
| A'-9 | 10 | 95 | 65 | 40 | 31 | 22 | 10 | 9 | 26 | 14 | 10 | 15 | 346 |
| A'-10 | 17.1 | 95 | 67 | 42 | 33 | 23 | 12 | 12 | 26 | 16 | 13 | 24 | 406 |
| A'-11 | 10 | 87.9 | 64 | 39 | 30 | 21 | 9 | 8 | 25 | 14 | 9 | 16 | 343 |
| A'-12 | 10 | 95 | 63 | 39 | 30 | 20 | 9 | 8 | 25 | 14 | 9 | 13 | 336 |
| A'-13 | 10 | 102.1 | 63 | 39 | 30 | 21 | 10 | 9 | 24 | 15 | 10 | 14 | 371 |
| A'-14 | 10 | 95 | 63 | 39 | 30 | 22 | 10 | 9 | 24 | 15 | 10 | 15 | 338 |
| A'-15 Comparative | 0 | 95 | 65 | 40 | 28 | 17 | 6 | 5 | 26 | 14 | 5 | 6 | 314 |

The results after aging at 148.9° C. (300° F.) demonstrate that the synergist-treated organoclay-containing mineral oil drilling fluid examples have much higher 6-RPM values than the control, but nearly identical 600-RPM values. The AHR-300 data showed the samples are useful up to at least 148.9° C. (300° F.). The data again showed an increase in low shear values and gel strength values as the level of Synergist A was increased when compared to the control sample.

A comparison of 600 RPM response (LVT-200 OBM) initially and after hot rolling at 121.1° C. (250° F.) for 16 hours for the organoclay processed at 95 MER alkyl quaternary ammonium compound with and without treatment by Synergist A at 10 weight % shows very little difference in all four values reported.

A comparison of 6 RPM response (LVT-200 OBM) initially and after hot rolling at 121.1° C. (250° F.) for 16 hours for the organoclay processed at 95 MER alkyl quaternary ammonium compound with and without 10% treatment by Synergist A can be made. The sample without Synergist A has a lower 6 rpm value in this OBM test both initially and AHR-250. Hot rolling at 121.1° C. (250° F.) did not have a significant effect, indicating sample/OBM stability.

Preparation of Organoclay B

Samples using Organoclay B, (B-2 to B-8), were made using various amounts of the alkyl quarternary ammonium salt 2M2HT and Synergist Solution B to treat a smectite (bentonite) clay by the dry-process method. Synergist Solution B was calculated and added "as is" to the clay on a dry weight (of clay) basis at the amounts (including carrier/solvent) indicated in Tables 12-14 and 16-18 for each organoclay sample. The alkyl quaternary ammonium (NR4+) addition was calculated on a dry weight of clay basis also at a specified MER indicated in Tables 12-14 and 16-18 for each organoclay sample. Synergist Solution B was comprised of about 75 weight percent of the subject synergist composition described in the preparation of Organoclay A, but in denatured alcohol as the carrier/solvent.

The general procedure was to first weigh 1000 g of milled bentonite "as is" into a plastic bag. The bentonite was then transferred to an Eirich mixer bowl and placed on an Eirich Mixer. Then, turning on circular motion only, Synergist Solution B and water (as needed) was added then mixed for 1 minute. The calculated amount of NR4+ was added, and the spindle mix was turned on for 2-3 minutes. Once complete, the mixer was turned off, the mixture removed, and the sides and bottom of the bowl were scraped to release any stuck material. Once complete, the bowl was returned to the Eirich mixer and again the circular and spindle functions of the mixer were turned on for 2-3 minutes. Again, when the mixer was turned off, the bowl was removed, and sides and bottom were scraped to remove all material, and the material was transferred to a pan.

The samples were finished with the use of a grinder, such as a conventional meat grinder. After placing a 24-hole die with a cutting blade at the discharge opening of the assembled grinder, the sample was added from the pan, adjusting the rate of discharge so that the grinder did not cease functioning, and this step was repeated until the entire sample had been through the grinder twice. Finally, the grinder was turned off, dissembled, and cleaned, collecting the material that was cleaned out of the grinder and adding it to the rest of the sample.

Organoclays B-1 through B-8 were tested in Drilling Fluid #3 according to the composition and mixing times described in Table 11. No synergist was added to the organoclay for the comparative example B-1.

TABLE 11

Drilling Fluid #3

| Material | Amount (grams per 350 ml) | Amount (grams per 420 ml) | Mixing time (Minutes) |
|---|---|---|---|
| Diesel #2 | 183 | 220 | n/a |
| Organoclay B | 6 | 7.2 | 5 |
| Lime | 3 | 3.6 | 5 |
| Emulsifier | 3.8 | 4.6 | 5 |
| 25% CaCl2 brine | 96.6 | 116 | 20 |
| Barite | 150 | 180 | 5 |
| OCMA clay | 20 | 24 | 5 |

After mixing all the components on the overhead mixer (Table 1), the samples were then sheared for 5-minutes on a Silverson mixer at 6,000 rpm to stabilize the emulsion. In order to test the viscosities of the various run samples, after mixing each OBM sample in a Silverson mixer the sample was transferred to a Thermo cup and placed on the OFITE 900 viscometer (a direct-indicating viscometer) and heated to 48.9° C. (120° F.). While heating, the viscometer was mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes was measured. The PV, YP, and ES were measured or calculated as described above.

Table 12 lists the results of initial viscosity testing as described above for the various organoclay B samples tested in Drilling Fluid #3.

Every synergist-treated sample showed improved initial performance over the comparative sample with regard to the 6 rpm, YP and GS values. Examples B-4, B-6, and B-8 had identical organoclay preparations (repeats) and the results show consistent performance. The synergist modification of the organoclay provided higher low shear values without a significant increase in high shear values, as was desired.

In order to obtain the AHR-150 and AHR-250 heat-aged samples, the OBM samples were returned to a mixing vessel, mixed with an overhead mixer, and then transferred into separate aging cells. For 121.1° C. (250° F.) hot rolling (AHR-250), the samples were placed in an appropriate aging cell; and 20.7 bar (300 psi) Nitrogen pressure was applied (apply 3×; release after first two charges and hold after third) on the aging cells to prevent volatilization of water in oil based fluid. Then, the samples were hot rolled at either 65.5° C. (150° F.) (AHR-150) or 121.1° C. (250° F.) (AHR-250), respectively, for 16 hours.

After removal of the samples following the hot rolling, the cells were air cooled and then vented to release any pressure from the cell as appropriate. The OBM samples were then transferred into the Thermo cup, placed on the OFITE 900 viscometer, and heated to 48.9° C. (120° F.) while mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes were measured. The PV, YP, and ES were measured or calculated as above.

Table 13 lists the results of AHR-150 viscosity testing as described above for the various organoclay B samples tested in Drilling Fluid #3.

TABLE 12

Initial Drilling Fluid #3 Results

| Ex. # | Organoclay B MER Quaternary NR4+ | % Synergist Solution | Dial Reading at Listed rpm | | | | | | PV | YP | GS 10" | 10' | ES |
|---|---|---|---|---|---|---|---|---|---|---|---|---|---|
| | | | 600 | 300 | 200 | 100 | 6 | 3 | | | | | |
| B-1 Comparative | 85 | 0 | 54.8 | 30.8 | 22.3 | 15.2 | 5.9 | 5.1 | 24 | 6.8 | 5 | 6 | 376 |
| B-2 | 90 | 12 | 64.1 | 40.2 | 30.2 | 21.3 | 10.5 | 9.7 | 23.9 | 16.3 | 10 | 11 | 579 |
| B-3 | 80 | 12 | 61.8 | 37.7 | 28.6 | 19.9 | 9.6 | 8.4 | 24.1 | 13.6 | 9 | 12 | 512 |
| B-4 | 85 | 8 | 64.2 | 41.3 | 30.2 | 21.1 | 9.9 | 9.1 | 22.9 | 18.4 | 9 | 11 | 510 |
| B-5 | 80 | 4 | 63.2 | 39 | 28.2 | 19.1 | 8.6 | 7.9 | 24.2 | 14.8 | 8 | 9 | 404 |
| B-6 | 85 | 8 | 64.2 | 40.2 | 30.3 | 21.6 | 10.8 | 10.1 | 24 | 16.2 | 10 | 12 | 469 |
| B-7 | 90 | 4 | 60.3 | 35.7 | 26.4 | 18.5 | 8.4 | 7.6 | 24.6 | 11.1 | 7 | 10 | 465 |
| B-8 | 85 | 8 | 63.2 | 40 | 29.2 | 20.2 | 9.7 | 8.8 | 23.2 | 16.8 | 9 | 10 | 476 |

TABLE 13

Drilling Fluid #3 Results AHR-150

| Ex. # | Organoclay B MER Quaternary NR4+ | % Synergist Solution | Dial Reading at Listed rpm | | | | | | PV | YP | GS | | ES |
|---|---|---|---|---|---|---|---|---|---|---|---|---|---|
| | | | 600 | 300 | 200 | 100 | 6 | 3 | | | 10" | 10' | |
| B-1 Comparative | 85 | 0 | 65 | 41 | 29.8 | 20 | 8.5 | 8 | 24 | 17 | 8 | 8 | 409 |
| B-2 | 90 | 12 | 85.3 | 56.2 | 43.7 | 29.5 | 12.3 | 11.5 | 29.1 | 27.1 | 12 | 18 | 662 |
| B-3 | 80 | 12 | 68.7 | 42.9 | 32.3 | 21.8 | 10.6 | 10.1 | 25.8 | 17.1 | 11 | 17 | 565 |
| B-4 | 85 | 8 | 70.5 | 45.2 | 33.2 | 22.9 | 10.9 | 10.8 | 25.3 | 19.9 | 11 | 14 | 561 |
| B-5 | 80 | 4 | 68 | 41.2 | 29.8 | 19.5 | 7.9 | 7.6 | 26.8 | 14.4 | 8 | 10 | 488 |
| B-6 | 85 | 8 | 67.2 | 42.6 | 31.3 | 21.5 | 10.4 | 9.7 | 24.6 | 18 | 10 | 14 | 625 |
| B-7 | 90 | 4 | 68.7 | 41.7 | 30 | 21.1 | 9 | 8.5 | 27 | 14.7 | 9 | 11 | 506 |
| B-8 | 85 | 8 | 68.9 | 44.3 | 31.7 | 21.8 | 10 | 9.4 | 24.6 | 19.7 | 9 | 13 | 572 |

Table 14 lists the results of AHR-250 viscosity testing as described above for the various organoclay B samples tested in Drilling Fluid #3.

Organoclay B samples were designated B'-1 through B'-8 to distinguish the test results in this drilling fluid. No synergist was added to the clay for the comparative example B'-1.

TABLE 14

Drilling Fluid #3 Results AHR-250

| Ex. # | Organoclay B MER Quaternary NR4+ | % Synergist Solution | Dial Reading at Listed rpm | | | | | | PV | YP | GS | | ES |
|---|---|---|---|---|---|---|---|---|---|---|---|---|---|
| | | | 600 | 300 | 200 | 100 | 6 | 3 | | | 10" | 10' | |
| B-1 Comparative | 85 | 0 | 61.8 | 40.8 | 29.8 | 20.1 | 7.8 | 7.3 | 21 | 19.8 | 7 | 7 | 404 |
| B-2 | 90 | 12 | 69.2 | 43.4 | 31.8 | 21.9 | 10.8 | 10.2 | 25.8 | 17.6 | 10 | 15 | 601 |
| B-3 | 80 | 12 | 64.3 | 40.6 | 29.8 | 19.9 | 9.4 | 9.1 | 23.7 | 16.9 | 9 | 12 | 511 |
| B-4 | 85 | 8 | 68.1 | 44.1 | 32.1 | 22.2 | 10.6 | 10.3 | 24 | 20.1 | 10 | 12 | 528 |
| B-5 | 80 | 4 | 60.7 | 37 | 26.5 | 18 | 7.2 | 6.7 | 23.7 | 13.3 | 6 | 8 | 429 |
| B-6 | 85 | 8 | 68.6 | 44.9 | 32.3 | 22.4 | 10.9 | 10.4 | 23.7 | 21.2 | 10 | 12 | 566 |
| B-7 | 90 | 4 | 63.7 | 39.6 | 29.3 | 19.6 | 9 | 8.5 | 24.1 | 15.5 | 8 | 10 | 422 |
| B-8 | 85 | 8 | 66.7 | 43.4 | 31.7 | 22.1 | 10 | 9.7 | 23.3 | 20.1 | 9 | 10 | 497 |

After hot rolling at 65.5° C. (150° F.), the Comparative Example B-1 yield result compares to the lowest level of synergist-treated samples. This demonstrates that the synergist modified organoclays yield faster than the control since they were better than the control initially. A faster yield means less energy is required to achieve desired performance. The higher level of synergist-treated samples performed better than the control throughout. The data also indicates that optimization through changes in the amount of quat and synergist can provide increased performance of the organoclay in this system.

The Organoclay B samples demonstrated very stable performance between initial, AHR-150, and AHR-250 testing. The organoclay samples with increasing synergist loading were progressively better than the control, showing higher low shear and gel strength values.

Treatment of the organoclay with the Synergist B composition has, as desired, little to no effect on the high shear viscosity.

An increase in 6 rpm dial readings was demonstrated for the Synergist B treated organoclay sample. This data clearly shows the organoclay control sample without treatment by Synergist B had a lower value than the sample of organoclay treated with Synergist B.

Organoclay B samples (B-1 through B-8) were also tested in Drilling Fluid #4, an LVT-200 base fluid, according to the composition and mixing times described in Table 15. The

TABLE 15

Drilling Fluid #4

| Material | Amount (grams per 350 ml) | Amount (grams per 420 ml) | Mixing time (Minutes) |
|---|---|---|---|
| LVT-200 | 179 | 215 | n/a |
| Organoclay B' | 10 | 12 | 5 |
| Lime | 3.0 | 3.6 | 5 |
| EnvaMul 1699 | 4.0 | 4.6 | 5 |
| 25% CaCl2 brine | 97 | 116 | 20 |
| Barite | 156 | 187 | 5 |
| OCMA Clay | 20 | 24 | 5 |

After mixing all the components on the overhead mixer (Table 1), the samples were then sheared for 5 minutes on a Silverson mixer at 6,000 rpm to stabilize the emulsion. In order to test the viscosities of the various run samples, after mixing each OBM sample in a Silverson mixer the sample was transferred to a Thermo cup and placed on the OFITE 900 viscometer (a direct-indicating viscometer) and heated to 48.9° C. (120° F.). While heating, the viscometer was mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes was measured. The PV, YP, and ES were measured or calculated as described above.

Table 16 lists the results of initial viscosity testing as described above for the various organoclay B' samples tested in Drilling Fluid #4.

TABLE 16

Initial Drilling Fluid #4 Results

| | Organoclay B' | | | | | | | | | | | | |
|---|---|---|---|---|---|---|---|---|---|---|---|---|---|
| | MER Quaternary | % Synergist | Dial Reading at Listed rpm | | | | | | | | GS | | |
| Ex. # | NR4+ | Solution | 600 | 300 | 200 | 100 | 6 | 3 | PV | YP | 10" | 10' | ES |
| B'-1 Comparative | 85 | 0 | 57.8 | 33 | 22.8 | 14.6 | 4.3 | 3.7 | 24.8 | 8.2 | 4 | 5 | — |
| B'-2 | 90 | 12 | 70.9 | 44.3 | 33.7 | 22.8 | 11.6 | 11.2 | 26.6 | 17.7 | 12 | 19 | — |
| B'-3 | 80 | 12 | 69.4 | 44.7 | 32.7 | 22.9 | 11.3 | 10.7 | 24.7 | 20 | 12 | 18 | — |
| B'-4 | 85 | 8 | 65.3 | 39.8 | 29.5 | 19.7 | 8.5 | 7.9 | 25.5 | 14.3 | 9 | 12 | — |
| B'-5 | 80 | 4 | 58.7 | 35.8 | 27.2 | 18.2 | 7.5 | 6.9 | 22.9 | 12.9 | 7 | 9 | — |
| B'-6 | 85 | 8 | 62.1 | 38.6 | 30 | 20.4 | 9.3 | 8.4 | 23.5 | 15.1 | 9 | 13 | — |
| B'-7 | 90 | 4 | 66.7 | 40.4 | 29.5 | 19.6 | 7.7 | 7.2 | 26.3 | 14.1 | 7 | 9 | — |
| B'-8 | 85 | 8 | 65.3 | 38.6 | 28.1 | 18.9 | 8.5 | 7.7 | 26.7 | 11.9 | 8 | 11 | — |

All of the organoclay B' samples, B'-2 through B'-8, prepared with synergist B showed higher low shear values and gel strength than the comparative example, B'-1, with no synergist. There is a trend for higher low shear values with higher synergist B levels. There was minimal effect on the high shear values as desired.

In order to obtain the AHR-150 and AHR-250 heat-aged samples, the OBM samples were returned to a mixing vessel, mixed with an overhead mixer, and then transferred into separate aging cells. For 121.1° C. (250° F.) hot rolling (AHR-250), the samples were placed in an appropriate aging cell; and 20.7 bar (300 psi) Nitrogen pressure was applied (apply 3×; release after first two charges and hold after third) on the aging cells to prevent volatilization of water in oil based fluid. Then, the samples were hot rolled at either 65.5° C. (150° F.) (AHR-150) or 121.1° C. (250° F.) (AHR-250), respectively, for 16 hours.

After removal of the samples following the hot rolling, the cells were air cooled and then vented to release any pressure from the cell as appropriate. The samples were mixed for 5 minutes with an overhead mixer. Then the OBM samples were transferred into the Thermo cup, placed on the OFITE 900 viscometer, and heated to 48.9° C. (120° F.) while mixing at 600 rpm. Once the desired temperature was reached, dial readings were taken at 600 rpm, 300 rpm, 200 rpm, 100 rpm, 6 rpm, and 3 rpm. Then, the GS at 10 seconds and 10 minutes were measured. The PV, YP, and ES were measured or calculated as above.

Table 17 lists the results of AHR-150 viscosity testing as described above for the various organoclay B' samples tested in Drilling Fluid #4.

TABLE 17

Drilling Fluid #4 Results AHR-150

| | Organoclay B' | | | | | | | | | | | | |
|---|---|---|---|---|---|---|---|---|---|---|---|---|---|
| | MER Quaternary | % Synergist | Dial Reading at Listed rpm | | | | | | | | GS | | |
| Ex. # | NR4+ | Solution | 600 | 300 | 200 | 100 | 6 | 3 | PV | YP | 10" | 10' | ES |
| B'-1 Comparative | 85 | 0 | 63.2 | 36.7 | 25.9 | 16.8 | 5.4 | 4.7 | 26.5 | 10.2 | 5 | 5 | 282 |
| B'-2 | 90 | 12 | 78.7 | 47.3 | 34.1 | 22.8 | 11.1 | 10.9 | 31.4 | 15.9 | 12 | 25 | 462 |
| B'-3 | 80 | 12 | 71.6 | 41.9 | 29.5 | 19.2 | 8.9 | 8.7 | 29.7 | 12.2 | 10 | 24 | 391 |
| B'-4 | 85 | 8 | 65 | 39.4 | 29.3 | 19 | 8.1 | 7.7 | 25.6 | 13.8 | 9 | 16 | 372 |
| B'-5 | 80 | 4 | 63.9 | 39.3 | 27.2 | 17.6 | 6.7 | 6.2 | 24.6 | 14.7 | 7 | 10 | 337 |
| B'-6 | 85 | 8 | 68.9 | 40.2 | 28.3 | 18.8 | 8.3 | 8 | 28.7 | 11.5 | 9 | 15 | 379 |
| B'-7 | 90 | 4 | 66.1 | 40.4 | 29.6 | 19.4 | 7.8 | 7.2 | 25.7 | 14.7 | 8 | 10 | 375 |
| B'-8 | 85 | 8 | 66.5 | 41.8 | 30.3 | 19.7 | 8.8 | 8.3 | 24.7 | 17.1 | 9 | 15 | 398 |

Table 18 lists the results of AHR-250 viscosity testing as described above for the various organoclay B' samples tested in Drilling Fluid #4.

TABLE 18

Drilling Fluid #4 Results AHR-250

| Ex. # | Organoclay B' | | Dial Reading at Listed rpm | | | | | | PV | YP | GS | | ES |
|---|---|---|---|---|---|---|---|---|---|---|---|---|---|
| | MER Quaternary NR4+ | % Synergist Solution | 600 | 300 | 200 | 100 | 6 | 3 | | | 10" | 10' | |
| B'-1 Comparative | 85 | 0 | 63.8 | 39 | 28.5 | 18.5 | 6.4 | 5.6 | 24.8 | 14.2 | 6 | 6 | 288 |
| B'-2 | 90 | 12 | 80 | 52.2 | 40.1 | 28.4 | 15 | 14.5 | 27.8 | 24.4 | 17 | 32 | 452 |
| B'-3 | 80 | 12 | 74.5 | 47.5 | 37.2 | 25.7 | 13.4 | 13 | 27 | 20.5 | 15 | 33 | 397 |
| B'-4 | 85 | 8 | 70.9 | 46.1 | 34.7 | 23.6 | 11.4 | 11.1 | 24.8 | 21.3 | 12 | 19 | 374 |
| B'-5 | 80 | 4 | 64.4 | 39.6 | 29.6 | 19.5 | 7.9 | 7.4 | 24.8 | 14.8 | 8 | 10 | 298 |
| B'-6 | 85 | 8 | 68.1 | 42.6 | 33.3 | 23.1 | 11.2 | 10.7 | 25.5 | 17.1 | 11 | 17 | 369 |
| B'-7 | 90 | 4 | 67.6 | 41.2 | 32 | 22.2 | 9.8 | 9 | 26.4 | 14.8 | 9 | 12 | 351 |
| B'-8 | 85 | 8 | 66.5 | 40.6 | 31.8 | 22.2 | 10.4 | 9.8 | 25.9 | 14.7 | 10 | 16 | 377 |

The low shear values and gel strength values for the comparative organoclay sample B'-1 was still lower than the values achieved by the synergist-treated organoclay samples B'-2 through B'-8, after aging. The change in the viscosity values due to aging was within acceptable limits for drilling fluids. One skilled in the art will recognize that the synergist-treated organoclays were more efficient than the organoclay without the synergist at generating rheological properties in a drilling fluid.

The results show little difference in the 600 rpm values for the OBM containing organoclay with and without Synergist B initially and after aging, as desired.

An increase in 6 rpm dial readings was demonstrated for the Synergist B treated organoclay sample. This data clearly shows the organoclay control sample without treatment by Synergist B had a lower value than the sample of organoclay treated with Synergist B.

Use of the Organocaly According to the Invention in Other Fluids

In another illustrative use, organoclays are used to suspend high concentrations of hydrophilic polymers in non-aqueous fluids. These concentrated fluids are referred to as polymer slurries. These polymer slurries are useful in industries such as gas and oil production to provide a means of delivering high concentrations of pre-dispersed hydrophilic polymer(s) for use in various applications, including without limitation, hydraulic fracturing fluid, gelling agents, buffers, lubricants, and non-emulsifiers/surfactants. Polymer slurries, as compared to dry hydrophilic polymer addition, prevent dusting, improve metering and improve ease of dispersion by eliminating "fish eyes" when used as a thickener in water or brine solutions, such as hydraulic fracturing, completion, or water based drilling fluids.

Examples of hydrophilic polymers include, without limitation, guar gum, xanthan gum, diutan gum, or modified starches. Guar gum is frequently used to thicken water to provide suspension properties for propping agents or proppants used in hydraulic fracturing fluids.

Guar slurries prepared with organoclays offer superior suspension and reduction of top oil separation. The organoclays produced with the disclosed synergist(s) provide even less separation of top oil. In order to test this property, a guar slurry was prepared using the following formula and mixing procedure. The guar slurry formula was 52.2% by weight of ODC mineral oil, 46.2% guar gum powder, 1.2% Organo-clay C, and 0.4% surfactant which was a wetting and dispersing agent for the hydrophilic polymer. The mixing procedure was: Organoclay C was added to the mineral oil and mixed for 1 minute, next the surfactant was added and mixed for 4 minutes, and finally the guar gum powder was added and mixed for 5 minutes. All mixing used a Dispermat mixer at 1,500 rpm.

Preparation of Organoclay C

Samples of Organoclay C (C-1 through C-7) were made using standard organoclay preparation techniques well-known in the art, by treating the clay with the alkyl quaternary ammonium salt 2M2HT, and Synergist Solution A. The comparative sample (C-8) did not have any synergist. First, the calculated amount of refined, MG sheared smectite (montmorillonite) slurry was weighed and added to the mixing vessel to achieve 60 grams of smectite on a dry weight basis, and mixing began while bringing the mixture to temperature (about 60-65° C.). Then, the synergist was added as indicated for each sample C1 through C7 in Table 19, except for comparative sample C8, while continuing to mix for 2-3 minutes. Then the quaternary ammonium compound (NH4+) was added based on the amount indicated for each sample in Table 19, allowing 30-45 minutes for reaction while mixing and scraping the sides of the vessel at least 3 times during mixing. Next, samples were filtered and placed in a blower oven overnight at 62.5° C. Finally, the samples were milled in a Retsch mill using a 0.2 screen and allowed to rehydrate overnight before testing.

These samples were prepared with varying amounts of quaternary NH4+ and Synergist Solution A as follows, in order to demonstrate the effectiveness in top oil suspension of Organoclay C:

TABLE 19

Organoclay C Compositions

| Organoclay C Sample | % quaternary NH4+ | Synergist Solution A |
|---|---|---|
| C-1 | 115 | 5 |
| C-2 | 105 | 10 |
| C-3 | 115 | 15 |
| C-4 | 105 | 10 |
| C-5 | 95 | 5 |
| C-6 | 105 | 10 |
| C-7 | 95 | 15 |
| C-8 (Comparative) | 105 | 0 |

Guar slurries were prepared with each organoclay sample, C-1 through C-8, according to the formula and mixing procedure set out above. Then, the viscosity of each guar slurry was measured in a Fann-35 viscometer at 300 rpm at ambient temperature (~75° F.). The guar slurries' viscosities varied between 195-220 cps, indicating they were pumpable fluids. There was minimal variation in viscosity at this high shear rate. Results of the tests described in this Example are reported in Table 20 below. Next, the viscosity of each guar slurry was measured using a Brookfield LVT viscometer for lower shear ranges. The results show an increase in low shear viscosity as the amount of Synergist A increases, which tends to improve suspension properties. After this viscosity testing, the samples were remixed, transferred to individual 100 ml graduated cylinders, and then stored, undisturbed at room temperature for 1 week. The top oil separation of each guar slurry, reported as a percentage (%), was measured over the span of one week.

TABLE 20

Guar Slurry Performance with Organoclay C

| Organoclay C | Fann-35 Viscosity 300 rpm | Brookfield Viscosity | | Top Oil Separation, % | | |
|---|---|---|---|---|---|---|
| | | 0.3 rpm | 100 rpm | 1-day | 4-day | 7-day |
| C-1 | 195 | 2,000 | 430 | 1 | 4 | 15 |
| C-2* | 204 | 2,667 | 476 | 1 | * | * |
| C-3 | 210 | 6,667 | 590 | 1 | 2 | 6 |
| C-4 | 209 | 4,000 | 514 | 1 | 3 | 10 |
| C-5 | 207 | 1,333 | 450 | 1 | 3 | 6 |
| C-6 | 198 | 3,333 | 524 | 1 | 3 | 11 |
| C-7 | 219 | 4,667 | 596 | 1 | 2 | 7 |
| C-8 comparative | 196 | 2,000 | 454 | 1 | 4 | 18 |

*Sample C-2 container leaked and the sample was therefore discarded

After Day 1, there was no significant difference among the samples (after 24 hours). After Day 4, the suspension properties were still fairly similar. Organoclay Sample C-2 vessel displayed a leak at this point, and therefore the sample and its evaluation was discarded. Since this was one of the repeat organoclays, the test was not repeated on this organoclay. After Day 7, the performance differences were apparent. The average value of the top oil separation, (%) after 7-days for the two repeat organoclay samples (C-4 and C-6) shows a general trend where the 7-day top oil separation % decreases, which is desired, as the amount of Synergist A increases. The data indicate that varying the amount of Synergist A and MER may be used to optimize an organoclay for specific applications.

The invention claimed is:

1. An organoclay composition comprising a mineral clay which has been treated with at least one organic quaternary ammonium or phosphonium compound or a precursor thereof and a synergist comprising (i) an amine salt of a trimer acid, the trimer acid having from about 30 to about 72 carbon atoms; and (ii) an amine salt of a monocarboxylic fatty acid, the monocarboxylic fatty acid having from about 6 to about 30 carbon atoms.

2. The organoclay composition of claim 1, wherein the monocarboxylic fatty acid is a tall oil fatty acid having from about 16 to about 22 carbon atoms.

3. The organoclay composition of claim 1, wherein the amine of the synergist component (i) and/or component (ii) is a saturated or unsaturated monoamine having from about 3 to about 90 carbon atoms.

4. The organoclay composition of claim 1, wherein the amine of the synergist component (i) and component (ii) are the same.

5. The organoclay composition of claim 1, wherein the amine comprises a monoamine of the general formula (I):

wherein:
$R^1$ represents a saturated or unsaturated, linear or branched hydrocarbon group having from about 1 to about 30 carbon atoms; and
$R^2$ and $R^3$ are the same or different from each other and R', and represent hydrogen or saturated or unsaturated, linear or branched hydrocarbon groups having from about 1 to about 30 carbon atoms.

6. The organoclay composition of claim 1, wherein the amine comprises at least one of n-propylamine, isopropylamine, n-butylamine, isobutylamine, amylamine, n-pentylamine, isopentylamine, hexylamine, 2-ethylhexylamine, octyl-amine, 6-methyl-2-heptaneamine, neopentylamine, decyl-amine, tridecylamine, octadecylamine, oleylamine, cocoyl amine, stearyl amine, tallow amine, soya amine, or mixtures of $C_8$-$C_{22}$ alkylamines.

7. The organoclay composition of claim 1, wherein the weight ratio of the synergist component (i):component (ii) is from about 95:5 to about 5:95.

8. The organoclay composition of claim 1, wherein the amount of synergist used to treat the clay mineral material ranges from about 2 to about 30 grams, based upon 100 grams of the dry mineral clay or mineral clay mixture.

9. The organoclay composition of claim 1, wherein the synergist is used in a liquid formulation which further comprises at least one additional material.

10. The organoclay composition of claim 1, wherein the mineral clay comprises at least one of a smectite clay; a hormite clay; a mixture of hormite clay and smectite clay; illite; vermiculite; or zeolites.

11. The organoclay composition of claim 10, wherein the smectite clay is selected from the group consisting of hectorite, montmorillonite, bentonite, beidellite, saponite, stevensite, Fuller's earth and mixtures thereof.

12. The organoclay composition of claim 1 wherein the phosphonium cation has the structure $R^1P^+(R^2)_3$ wherein $R^1$ is a $C_8$ to $C_{24}$ alkyl or arylalkyl group and each $R^2$, which may be the same or different, is an aryl, arylalkyl, or a $C_1$ to $C_6$ alkyl group; and wherein the counter-ion is at least one of chloride, bromide, iodide, sulfate, methoxysulfate, methyl sulfate, ethyl sulfate, sulfonate, phosphate, phosphonate, phosphite, carboxylate, or acetate.

13. The organoclay composition of claim 1, wherein the alkyl or alkenyl quaternary ammonium compound comprises a salt having formula (IIa):

wherein N is nitrogen; $R^5$, $R^6$, $R^7$ and $R^8$ are independently selected from the group consisting of (a) linear or branched, saturated or unsaturated alkyl groups having 1 to 22 carbon atoms, (b) aralkyl groups which are benzyl and substituted benzyl moieties, (c) aryl groups, (d) beta, gamma-unsaturated groups having six or less carbon atoms or hydroxyalkyl groups having two to six carbon atoms, and (e) hydrogen, with the proviso that at least one of the substituents is a linear or branched unsaturated alkyl group; and X is a salt anion.

14. The organoclay composition of claim 1, wherein the organic quaternary ammonium compound comprises an alkoxylated quaternary ammonium salt having formula (III):

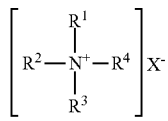

(III)

wherein N is nitrogen; X" comprises an anion comprising at least one of chloride, sulfate, methyl sulfate, ethyl sulfate, acetate, iodide, bromide, nitrate, hydroxide, phosphate, methoxysulfate and mixtures thereof; le comprises a $C_{12}$ to $C_{30}$ linear or branched, saturated or unsaturated alkyl or alkenyl group, or alkyl-ester groups having 8 to 30 carbon atoms; $R^2$ comprises H— or a $C_1$ to $C_{30}$ linear or branched, saturated or unsaturated alkyl or alkenyl group; $R^3$ comprises H—, $C_1$ to $C_4$ linear or branched, saturated or unsaturated alkyl or alkenyl group or $R^4$; and, $R^4$ comprises —$(CR^9R^{10}$— $CR^{11}R^{12}O)_yH$, or —$(CR^9R^{10}$—$CR^{11}R^{12}$—$CR^{13}R^{14}O)_yH$, where $R^9$, $R^{10}$, $R^{12}$, $R^{13}$ and $R^{14}$ are independently selected from the group consisting of H—, $CH_3$—, and $CH_3CH_2$— and y is 4 to about 20 on average.

15. The organoclay composition of claim 14, wherein the alkoxylated quaternary ammonium salt comprises at least one of methyl bis(polyoxyethylene [15])cocoalkyl quaternary ammonium salt, methyl bis(polyoxyethylene [15])oleyl quaternary ammonium salt, methyl bis(polyoxyethylene [15])octadecyl quaternary ammonium salt, or octadecylmethyl [polyoxyethylene (15)] quaternary ammonium salt, or mixtures thereof, wherein the numbers in brackets refer to the total number of ethylene oxide units.

16. The organoclay composition of claim 1, wherein the total amount of organic cation or blends of different cations added to the mineral clay or mineral clay mixture from the quaternary ammonium or phosphonium compound is 75%-230% of the CEC of the base mineral clay or mineral clay mixture.

17. The organoclay composition of claim 1, wherein the mineral clay or mineral clay mixture is treated with about 15 to about 160 milliequivalents of the organic quaternary ammonium salt per 100 g of the mineral clay or mineral clay mixture.

18. A drilling fluid comprising a hydrocarbon-based or invert emulsion drilling fluid based composition, and the organoclay composition of claim 1.

19. The drilling fluid of claim 18, comprising from about 2.85 to about 42.80 kg/m³ (about 1 to about 15 lbs/barrel) of the organoclay composition.

20. The drilling fluid of claim 18, wherein the base fluid comprises at least one of diesel oil, mineral oil, mineral seal oil, kerosene, fuel oil, white oil, crude oil, synthetic oil, natural oil, alpha olefins, poly alpha olefins, linear alpha olefins, internal olefins, linear paraffins, linear alkyl benzene and biodegradable oils.

21. The drilling fluid of claim 18, having an Oil/Water Ratio by volume (OWR) of about 95/5 to about 40/60.

22. The drilling fluid of claim 18, wherein the water of the aqueous internal phase is a brine.

23. The drilling fluid of claim 18, further comprising at least one of an emulsifier, a wetting agent, an acid gas scavenger, a weighting agent, a fluid loss control additive, a bridging agent, an alkalinity control agent, a material that imparts alkalinity, a non-clay rheological additive, and/or a corrosion inhibitor.

24. A composition comprising the organoclay composition of claim 1, wherein the composition is selected from a grease composition, a paint formulation, a coating formulation, an adhesive formulation, an unsaturated polyester composition, a lubricant, a metal working fluid, an ink, a sealant, a vinyl ester system, an acrylic resin system, an epoxy resin system, a polyurethane resin system, a nanocomposite, a mastergel, a moulding compound, a cosmetic composition, a cleaner, a personal care formulation, and a home care formulation.

25. A hydrophilic polymer slurry in a nonaqueous fluid, comprising the organoclay composition of claim 1.

* * * * *